United States Patent
Pierce, II et al.

(10) Patent No.: US 12,377,289 B2
(45) Date of Patent: Aug. 5, 2025

(54) DEVICES, SYSTEMS, AND METHODS FOR PERSONALIZED DOSIMETRY

(71) Applicant: University of Washington, Seattle, WA (US)

(72) Inventors: Larry A Pierce, II, Seattle, WA (US); Robert S. Miyaoka, Seattle, WA (US); Robert L Harrison, Seattle, WA (US)

(73) Assignee: University of Washington, Seattle, WA (US)

( * ) Notice: Subject to any disclaimer, the term of this patent is extended or adjusted under 35 U.S.C. 154(b) by 202 days.

(21) Appl. No.: 18/035,612

(22) PCT Filed: Nov. 5, 2021

(86) PCT No.: PCT/US2021/058270
§ 371 (c)(1),
(2) Date: May 5, 2023

(87) PCT Pub. No.: WO2022/099020
PCT Pub. Date: May 12, 2022

(65) Prior Publication Data
US 2024/0066322 A1     Feb. 29, 2024

Related U.S. Application Data

(60) Provisional application No. 63/110,780, filed on Nov. 6, 2020.

(51) Int. Cl.
*A61B 5/00* (2006.01)
*A61B 6/00* (2024.01)
(Continued)

(52) U.S. Cl.
CPC .......... *A61N 5/1071* (2013.01); *A61B 5/6805* (2013.01); *A61B 6/032* (2013.01);
(Continued)

(58) Field of Classification Search
CPC .............................. A61B 5/6805; A61B 6/032
See application file for complete search history.

(56) References Cited

U.S. PATENT DOCUMENTS

| | | | |
|---|---|---|---|
| 5,803,089 | A | 9/1998 | Ferre et al. |
| 6,381,482 | B1 | 4/2002 | Jayaraman et al. |

(Continued)

FOREIGN PATENT DOCUMENTS

| | | |
|---|---|---|
| CA | 2941409 A1 | 9/2014 |
| CN | 109523586 A | 3/2019 |

(Continued)

OTHER PUBLICATIONS

Calais and Turner, "Outpatient 131I-rituximab radioimmunotherapy for non-Hodgkin lymphoma: a study in safety," Clin Nucl Med, vol. 37, No. 8, pp. 732-737.

(Continued)

*Primary Examiner* — Dani Fox
(74) *Attorney, Agent, or Firm* — Katherine M. Mead; Lee & Hayes PC

(57) ABSTRACT

Various devices, systems, and methods for performing personalized dosimetry of a patient receiving a radiopharmaceutical are described. In an example method, anatomic data is generated by performing a computed tomography (CT) scan on the patient when they are lying down and wearing a garment. Based on the anatomic data, locations of organs of the patient are determined with respect to one or more fiducial markers integrated with the garment. Detectors for detecting photons from a radiopharmaceutical are placed on the garment based on locations of the organs. Subsequently, the patient may be administered a dose of the radiopharmaceutical. When the patient wears the garment, the detectors may detect photons released from the decaying radiopharmaceutical that is distributed in the organs. The radiation (Continued)

dosage to the organs may be determined based on the detected photons.

20 Claims, 7 Drawing Sheets

(51) Int. Cl.

| | | |
|---|---|---|
| A61B 6/03 | (2006.01) | |
| A61B 6/04 | (2006.01) | |
| A61B 6/42 | (2024.01) | |
| A61N 5/10 | (2006.01) | |

(52) U.S. Cl.
CPC ............ *A61B 6/037* (2013.01); *A61B 6/0407* (2013.01); *A61B 6/4266* (2013.01)

(56) References Cited

U.S. PATENT DOCUMENTS

| | | | |
|---|---|---|---|
| 9,002,438 | B2 | 4/2015 | Knowland et al. |
| 9,314,160 | B2 | 4/2016 | Adler, Jr. et al. |
| 9,939,533 | B2 | 4/2018 | Knowland et al. |
| 10,029,120 | B2 | 7/2018 | Schulz et al. |
| 10,852,446 | B2 | 12/2020 | Knowland et al. |
| 2003/0193032 | A1 | 10/2003 | Marshall |
| 2004/0008810 | A1 | 1/2004 | Nelson et al. |
| 2004/0236207 | A1 | 11/2004 | Widener et al. |
| 2006/0027756 | A1 | 2/2006 | Thomson et al. |
| 2007/0265230 | A1 | 11/2007 | Rousso et al. |
| 2009/0145655 | A1 | 6/2009 | Gladd et al. |
| 2010/0322854 | A1 | 12/2010 | Low et al. |
| 2011/0208044 | A1 | 8/2011 | Edwards et al. |
| 2012/0080602 | A1 | 4/2012 | Garcia Diego et al. |
| 2012/0148132 | A1 | 6/2012 | Couch et al. |
| 2013/0218001 | A1 | 8/2013 | Uhlemann |
| 2014/0088401 | A1 | 3/2014 | Cai et al. |
| 2014/0275939 | A1 | 9/2014 | Mitteldorf |
| 2015/0247933 | A1 | 9/2015 | McQuirter et al. |
| 2015/0301204 | A1 | 10/2015 | Srivastava et al. |
| 2016/0103227 | A1 | 4/2016 | Beddar et al. |
| 2016/0259063 | A1 | 9/2016 | Lee et al. |
| 2017/0086763 | A1 | 3/2017 | Verma et al. |
| 2017/0219720 | A1 | 8/2017 | Cortesi et al. |
| 2017/0319155 | A1 | 11/2017 | Rubenstein et al. |
| 2018/0092698 | A1* | 4/2018 | Chopra .................. A61B 90/39 |
| 2018/0193666 | A1 | 7/2018 | Zhang et al. |
| 2019/0018148 | A1 | 1/2019 | Ueno et al. |
| 2020/0206534 | A1 | 7/2020 | Bzdusek |

FOREIGN PATENT DOCUMENTS

| | | |
|---|---|---|
| EP | 2967465 A1 | 1/2016 |
| EP | 3059612 A1 | 8/2016 |
| EP | 3432034 | 1/2019 |
| JP | 2013183756 A | 9/2013 |
| JP | 6377574 B2 | 12/2018 |
| JP | 6434206 B2 | 12/2018 |
| KR | 20200015208 A | 2/2020 |
| WO | WO2017115340 A1 | 7/2017 |
| WO | WO2018022990 A1 | 2/2018 |
| WO | WO2019099551 A1 | 5/2019 |
| WO | WO2019217928 A1 | 11/2019 |

OTHER PUBLICATIONS

D'Arienzo, et al., "90Y PET-based dosimetry after selective internal radiotherapy treatments," Nuclear Medicine Communications, vol. 33, No. 6, Jun. 2012, pp. 633-640.
Dewaraja, et al., "MIRD Pamphlet No. 23: Quantitative SPECT for Patient-Specific 3-Dimensional Dosimetry in Internal Radionuclide Therapy," Journal of Nuclear Medicine, vol. 53, No. 8, Aug. 1, 2012, 16 pages.
Fragogeorgi, et al., "Exploitation of SiPM technology for the developemnt of a Theranostic Imaging device," Journal of Nuclear Medicine, vol. 56 (supplement 3) 1841, May 2015, 4 pages.
Frezza, et al., "Validation of irtGPUMCD, a GPU-based Monte Carlo internal dosimetry framework for radionuclide therapy," Physica Medica, vol. 73, May 2020, pp. 95-104.
Goetz, et al., "Three-dimensional Monte Carlo-based voxel-wise tumor dosimetry in patients with neuroendocrine tumors who underwent Lu-DOTATOC therapy", Annals of Nuclear Medicine, Japanese Society of Nuclear Medicine, vol. 34, No. 4, Feb. 29, 2020, pp. 244-253.
Gregory, et al., "Standardised quantitative radioiodine SPECT/CT Imaging for multicentre dosimetry trials in molecular radiotherapy," Phys. Med. Biol., vol. 64, 245013, 2019, 15 pages.
Grimes, "Patient-specific internal dose calculation techniques for clinical use in targeted radionuclide therapy," 2013, 186 pages, obtained from https://open.library.ubc.ca/soa/cIRcle/collections/ubctheses/24/items/1.0073590.
Li, et al., "Fully-Depleted Silicon-on-Insulator Devices for Radiation Dosimetry in Cancer Therapy," IEEE Transactions on Nuclear Science, vol. 61, No. 6, Dec. 2014, pp. 3443-3450.
Li, et al., "Quantitative Imaging for Targeted Radionuclide Therapy Dosimetry—Technical Review," Theranostics, vol. 7, No. 18, 2017, pp. 4551-4565.
Ma, et al., "Clinical implementation of a Monte Carlo treatment planning system," Medical Physics, vol. 26, No. 10, Oct. 1999, pp. 2133-2143.
Malaroda, et al., "Multicellular Dosimetry in Voxel Geometry for Targeted Radionuclide Therapy," Cancer Biotherapy & Radiopharmaceuticals, vol. 18, No. 3, 2003, 11 pages.
Mijnheer, et al., "In vivo dosimetry in external beam radiotherapy," Med. Phys., vol. 40, No. 7, Jul. 2013, 19 pages.
Miyaoka, et al., "Wearable technology to enable personalization of Lu177-DOTATATE therapy for neuroendocrine tumor in patients", Journal of Nuclear Medicine, Mar. 7, 2019, pp. 1-4.
Nascimenti, et al., "Application of Al2O3:C+fibre dosimeters for 290 MeV/n carbon therapeutic beam dosimetry," Radiation Physics and Chemistry, vol. 115, Oct. 2015, pp. 75-80.
Nascimento, et al., "Medical dosimetry using a RL/OSL prototype," Radiation Measurements, vol. 71, Dec. 2014, pp. 359-363.
Nuclear Medicine/Radiopharmaceuticals Market by Type & by Application : Global Forecasts to 2021. MarketsandMarkets [internet]. [cited Dec. 29, 2017] obtained from: https://www.marketsandmarkets.com/Market-Reports/radiopharmaceuticals-market-417.html.
Obenaus and Smith,. "Radiation Dose in Rodent Tissues During micro-CT Imaging", Journal of X-Ray Science and Technology, vol. 12, No. 4, 2004, pp. 241-249.
Osovisky, et al., "SENTIRAD—An innovative personal radiation detector based on a scintillation detector and a silicon photomultiplier," Nuclear Instruments and Methods in Physics Research Section A: Accelerators, Spectrometers, Detectors and Associated Equipment, vol. 652, No. 1, Oct. 1, 2011, pp. 41-44.
Park, et al., "Development of a Portable Device Based Wireless Medical Radiation Monitoring System," Journal of Radiation Protection and Research, vol. 39, No. 3, 2014, pp. 150-158.
Perks, 2008, "Medical dosimetry using optically stimulated luminescence dots and microStar readers". 12. International congress of the International Radiation Protection Association (IRPA): Strengthening radiation protection worldwide (IRPA 12), SAR.
Perrot, et al., "Internal dosimetry through Gate simulations of preclinical radiotherapy using a melanin-targeting ligand," Phys. Med. Biol., vol. 59, 2014, pp. 2183-2198.
Petitguillaume, et al., "Three-Dimensional Personalized Monte Carlo Dosimetry in 90Y Resin Microspheres Therapy of Hepatic Metastases: Nontumoral Liver and Lungs Radiation Protection Considerations and Treatment Planning Optimization," Journal of Nuclear Medicine, vol. 55, Issue 3, Mar. 1, 2014, 9 pages.
Pourhomayoun, et al., "Accurate tumor localization and tracking in radiation therapy using wireless body sensor networks," Comput Biol Med, vol. 50, Jul. 2014, pp. 41-48.

(56) References Cited

OTHER PUBLICATIONS

Prete, et al., "Personalized 177Lu-octreotate peptide receptor radionuclide therapy of neuroendocrine tumours: a simulation study," European Journal of Nuclear Medicine and Molecular Imaging, vol. 44, No. 9, pp. 1490-1500.

Prete, et al., "Personalized 177Lu-octreotate peptide receptor radionuclide therapy of neuroendocrine tumors: initial dosimetry and safety results of the P-PRRT trial," Journal of Nuclear Medicine, vol. 58 (supplement 1), No. 242, May 2017, 5 pages.

Prideaux, et al., "Three-Dimensional Radiobiologic Dosimetry: Application of Radiobiologic Modeling to Patient-Specific 3-Dimensional Imaging-Based Internal Dosimetry," Journal of Nuclear Medicine, vol. 48, Issue 6, Jun. 2007, 9 pages.

Radioisotope Therapy [internet]. Peter MacCallum Cancer Centre. [cited Dec. 28, 2017] obtained from: https://www.petermac.org/patients-and-carers/treatments/radioisotope-therapy.

Radiotherapy: Technologies and Global Markets. BCC Research [internet]. [cited Dec. 29, 2017] obtained from: https://www.bccresearch.com/market-research/healthcare/radiotherapy-technologies-markets-report.html.

Sarrabayrouse and Siskos, "Radiation dose measurment using MOSFETs," in IEEE Instrumentation & Measurement Magazine, vol. 1, No. 2, Jun. 1998, pp. 26-34.

Siegel, et al., "Cancer statistics," CA Cancer J Clin, vol. 69, 2019, pp. 7-34.

Search Report for European Application No. 21890157.7, Dated Aug. 19, 2024, 9 pages.

Surveillance and Monitoring of Explosive, Chemical, Biological, and Nuclear Hazards. BCC Research [internet]. [cited Dec. 29, 2017] obtained from: https://www.bccresearch.com/market-research/safety-and-security/ecbn-hazards.html.

Taylor, et al., "Proton tracking for medical imaging and dosimetry," Journal of Instrumentation, vol. 10, 2018, 15 pages.

Williams and Raymond, "Fiber-optic-coupled RbMgF3:Eu2+ for remote radiation dosimetry," Radiation Measurements, vol. 46, No. 10, Oct. 2011, pp. 1099-1102.

Williams, et al.,, "Towards real-time topical detection and characterization of FDG dose infiltration prior to PET imaging," Eur J Nucl Med Mol Imaging, vol. 43, No. 13, Aug. 25, 2016, pp. 2374-2380.

Woulfe, et al., "Optical fibre sensors: their role in in vivo dosimetry for prostate cancer radiotherapy," Cancer Nanotechnol., vol. 7, No. 1, Oct. 18, 2016, 16 pages.

Search Report and Written Opinion for PCT Application No. PCT/US21/58270, mailed Feb. 4, 2022, 17 pages.

\* cited by examiner

DEVICES, SYSTEMS, AND METHODS FOR PERSONALIZED DOSIMETRY

CROSS-REFERENCE TO RELATED APPLICATIONS APPLICATION

This application is a U.S. National Phase Application based on International Patent Application No. PCT/US2021/058270, filed on Nov. 5, 2021, which claims the priority of U.S. Provisional Application No. 63/110,780, which was filed on Nov. 6, 2020, each of which is incorporated by reference herein in its entirety.

STATEMENT REGARDING FEDERALLY SPONSORED RESEARCH OR DEVELOPMENT

This invention was made with government support under Grant No. R01 CA042593, awarded by the National Institutes of Health. The government has certain rights in the invention.

BACKGROUND

Radiation therapy uses ionizing radiation to kill cancer cells and shrink tumors by damaging the deoxyribonucleic acid (DNA) of the cells. One form of radiation therapy is external radiation therapy, wherein a limited area of the body is irradiated with a beam of x-rays that disrupt the cancer cells of the patient. Unsealed source radiotherapy (also referred to as "targeted radionuclide therapy," "unsealed source radionuclide therapy," and "molecular radiotherapy"), on the other hand, is a systemic treatment using a radiopharmaceutical including a cancer cell-targeting molecule combined or "labeled" with a radionuclide. The radiopharmaceutical is designed to deliver a toxic level of radiation to targeted disease sites. However, unlike tumor-directed chemotherapies and toxins that kill only the directly targeted cells, radionuclides may also destroy adjacent tumor cells even if they lack the specific tumor-associated antigen or receptor. A systemically administered targeted radiopharmaceutical may simultaneously eliminate both a primary tumor site and cancer that has spread throughout the body, including malignant cell populations undetectable by diagnostic imaging. In internal targeted radionuclide therapy the radiopharmaceutical is typically introduced into a subject by injection or ingestion. The cell-targeting molecule transports the radionuclide to a desired location, organ, or tissue, depending on the properties and administration of the radiopharmaceutical.

For example, peptide receptor radionuclide therapy (PRRT) is an unsealed source radiotherapy used for treating neuroendocrine tumors (NETs) wherein the radiopharmaceutical is a cell-targeting protein or peptide combined with a radionuclide. When injected into the bloodstream, the radio-peptide travels to and binds to NET cells, delivering a targeted high dose of radiation directly to the cancer cells. Octreotide (e.g., a component of DOTATOC), oxodotreotide, and octreotate (e.g., a component of DOTATATE, also referred to as DOTA-octreotate, oxodotreotide, DOTA-(Tyr$^3$)-Octreotate, and which is a peptide that with length of eight amino acides and a covalently bonded DOTA bifunctional chelator), for example, are laboratory-made versions of the hormone that binds to somatostatin receptors on NETs. In PRRT, the somatostatin analogue is combined with a therapeutic dose of the radionuclide. Yttrium-90 ($^{90}$Yt) and Lutetium-177 ($^{177}$Lu) are commonly used radionuclides for PRRT.

For patients with metastatic, somatostatin-receptor-2 (SSTR2) NETs, targeted therapy using $^{177}$Lu-DOTATATE has been found to greatly increase progression-free survival (PFS). Now that $^{177}$Lu-DOTATATE has been approved by the United States (US) Food and Drug Administration (FDA), it is quickly becoming the standard-of-care for symptomatic NET patients and those with metastatic spread.

$^{177}$Lu-DOTATATE is one example of a radiotherapy for PRRT. A protocol for PRRT may include administering a series of four treatments (e.g., $^{177}$Lu-DOTATATE treatments) spaced approximately two months apart. The treatments may be performed as an outpatient procedure, or as an inpatient procedure in which the patient stays in the hospital for several days. Each session may begin with providing an anti-nausea medicine, followed by an amino acid solution delivered intravenously. The radionuclide is then injected, followed by additional amino acid solution. $^{177}$Lu-DOTATATE US FDA package instructions call for patients to receive a standardized regimen of four 7.4 Gigabecquerel (GBq) treatments, regardless of size, weight, gender, or patient health status. Thus, the standard treatment is not personalized for individual patients.

Medical research is striving towards individualized therapies and precision treatments. For example, many patients can tolerate more than four treatments of $^{177}$Lu-DOTATATE. Studies show that personalized therapies can increase PFS and overall survival (OS) by over 100% if treatments continue until dosing to the kidneys reaches 23 Gray (Gy), which corresponds to a recognized ionizing radiation dose cutoff for the kidneys. Recent studies indicate that patients who continued to receive $^{177}$Lu-DOTATATE treatments until their kidney dose reached 23 Gy (i.e., 3 to 9 treatments) had >100% increase in PFS (i.e., 33 vs. 15 months) and OS (i.e., 54 vs. 25 months) than patients whose treatments stopped before their kidneys received 23 Gy. Furthermore, some patients may receive damaging levels of radiation to their kidneys (i.e., >23 Gy) if they receive the standardized four 7.4 GBq doses of $^{177}$Lu-DOTATATE. Knowing the actual dose to the kidneys is important because the kidneys are a main dose-limiting organ in 98% of patients. Other dose-limiting organs include the liver, spleen, and bone marrow. Tracking the radiation dosages to kidneys and other organs can prevent physicians from under-dosing or overdosing patients with radiotherapies.

Physicians are unable to track the radiation doses to the dose-limiting organs of patients without actively monitoring those organs. For example, the amount of ionizing radiation absorbed by the organs can be derived by performing multiple single-photon emission computed tomography (SPECT-CT) scans on the patient after treatment with a radiotherapy. A SPECT-CT scanner is configured to detect photons emitted by the radiotherapy as well as the anatomic structures of the patient. However, SPECT-CT imaging has a relatively high cost. SPECT-CT imaging is generally unavailable in community hospitals and may only be available at specialized medical centers. A patient seeking personalized dosimetry may have to travel a large distance to a research hospital in order to receive the necessary SPECT-CT scans. $^{177}$Lu-DOTATATE organ dosimetry is therefore uncommon in the US, even though personalized dosimetry could significantly improve patient outcomes. International Application No. PCT/US2019/031880, titled "Multi-Detector Personalized Home Dosimetry Garment," which is hereby incorporated by reference in its entirety, describes a garment for detecting radiation washout in organs. However, the use of the garment described in this reference involves the use of multiple SPECT-CT scans. For example, a patient may be subjected to one or more SPECT-CT scans per radiopharmaceutical dosage.

Practical tools are needed to accurately assess dose to the dose-limiting organs, and in particular the kidney. Treatment personalization has been shown to significantly improve outcomes over the standardized four-treatment protocol. Furthermore, a significant number of cancer patients can benefit from personalized treatments. In 2014, there were 171,000 NET patients with an estimated incidence rate of new cases of 6.98/100,000 per year (over 22,000 new patients). Eighty-one percent of NETs are SSTR2 positive. Accordingly, there is a significant need to improve $^{177}$Lu-DOTATATE dosimetry. In addition, the teachings disclosed herein will be applicable to other promising theranostics protocols currently under development.

For radionuclide theranostics (e.g., radiopharmaceuticals), there is benefit to monitor the levels of radiation in patient organs (e.g., organs at risk or "OARs") and in tumors in the patient's body, for days or weeks. Cancer cells overexpress the somatostatin receptor, which preferentially bind octreotide and target the radioactive compound directly at tumors. In addition to neuroendocrine tumors, PRRT and similar treatments using radioisotopes have been used to effectively treat bone metastases, thyroid cancers, and lymphomas.

One of the challenges associated with molecular radiotherapies is that patients can dramatically differ in their ability to absorb the radioactive molecules and/or in their ability to flush the radioactive molecules from their body. Knowing this, care providers may personalize treatments by monitoring the absorbed radiation dosage at both the tumor site and at dose-limiting organs. Unfortunately, repeated imaging of radionuclides is costly and time consuming for patients. There exists a great need to lessen the monitoring and treatment-adjusting burden on both patients and physicians, which can significantly improve quality of care, and quality of life, for patients.

DETAILED DESCRIPTION

Figure 1:
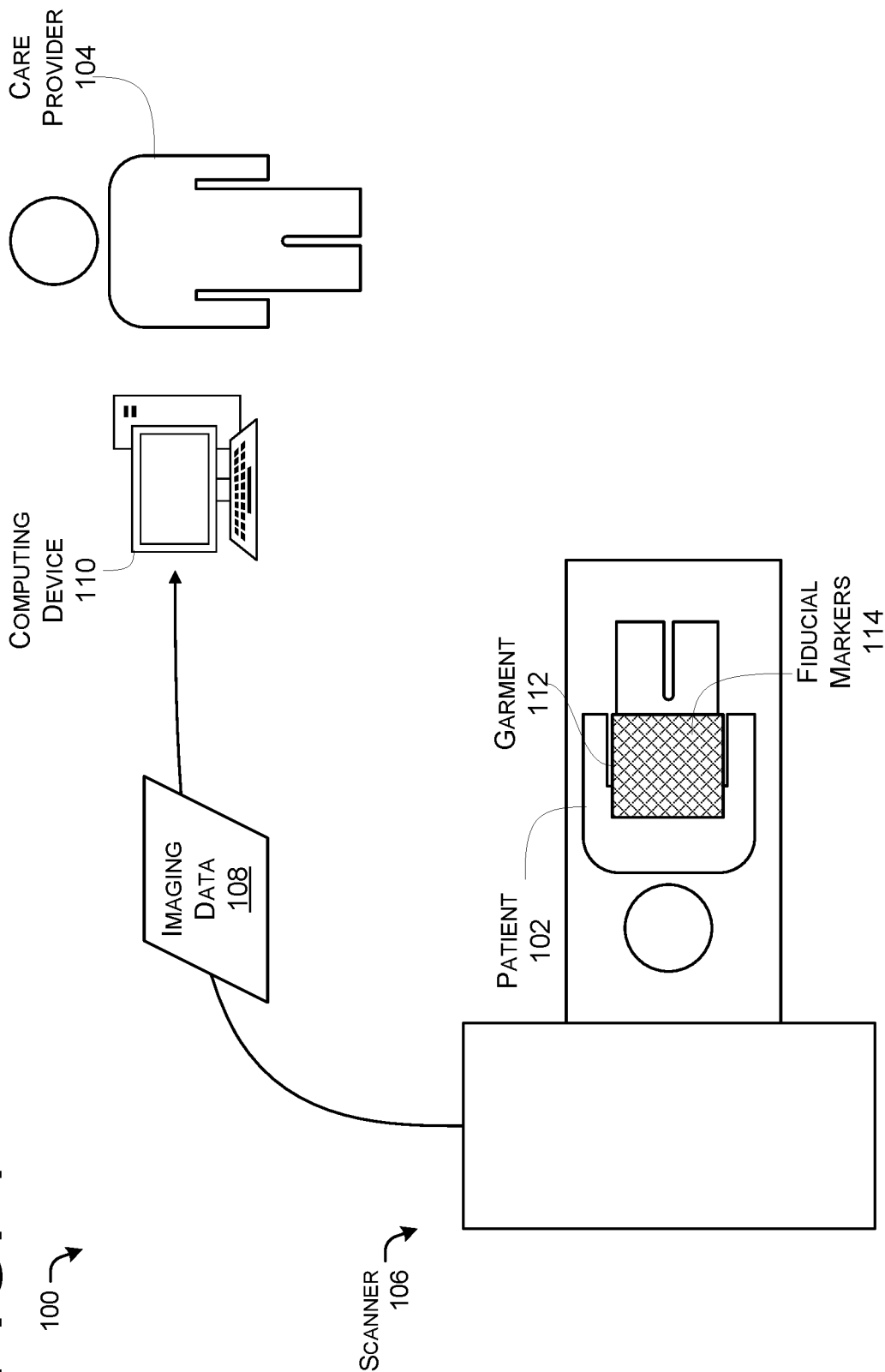
FIG. 1 illustrates an environment for optimizing detector positions to perform personalized dosimetry.

Various implementations described herein relate to techniques for achieving personalized dosimetry of patients being treated with radiopharmaceuticals. According to some examples, a garment is personalized for a particular patient based on at least one anatomic scan of that patient (e.g., a CT scan). In particular cases, a set of detectors are positioned on the garment based on the locations of organs and tumors within the patient's body. The patient may be administered a dose of a radiopharmaceutical. When the patient wears the garment, the detectors may detect photons emitted from the radiopharmaceutical. The garment may export data indicating the detected photons to an external device, which may determine the radiation dosage to each of the organs by the radiopharmaceutical based on the data. The external device may report the result of its analysis to a care provider, who may decide whether to administer an additional dose of the radiopharmaceutical based on the radiation dosage to each of the organs. In various cases, personalized dosimetry can be achieved without performing a quantitative SPECT-CT scan after the radiopharmaceutical is administered.

For some radiological procedures, a quantitative PET-CT or SPECT-CT scan is produced in order to check the quality of the radiological procedure. For example, prior to the administration of a radiotherapy, such as the course of $^{177}$Lu-DOTATATE administration outlined in International Application No. PCT/US2019/031880, a quantitative $^{68}$Ga-DOTATATE PET-CT scan of the patient may be taken in order to evaluate how effective a radiotherapy treatment may be expected to perform, as well as to locate items of importance (e.g. tumors, etc.) within the patient's anatomy. However, existing techniques also include performing one or more quantitative SPECT-CT scans after an administration of the radiotherapy to evaluate uptake of the radiotherapy by the therapy target, or to evaluate presence of the radiotherapy in regions other than the target site (e.g., in other organs).

In implementations described herein, an array of detectors (e.g., radiation sensors) are reproducibly placed near the body of a patient who has been administered a radionuclide as part of a radiotherapy. In some cases, the detectors are included in a garment worn by the patient, attached to the patient, placed within the body of the patient, or a combination thereof. In some cases, the sensors are mounted on a gantry and can be movable with respect to the body of the patient. The detectors are configured to detect photons emitted from the radionuclide. In addition, the locations of the organs (e.g., relative to the detectors) may be determined by an anatomic scan of the body of the patient. For example, a CT scan can be performed on the patient while the patient is wearing the garment. In some implementations, the CT scan is part of a PET-CT scan that is performed on the patient to identify whether the patient has cancer cells expressing a receptor of the radionuclide, or the CT scan may be an independent CT scan performed on the patient. Based on the locations of the detectors and the organs, as well as the photons detected by the detectors, a distribution of radiation within the organs during an acquisition time of the detectors can be determined. In addition, the radionuclide may have a known radioactive decay (e.g., a known half-life). Thus, the total radiation dosages to individual organs of the patient can be derived based on the distribution of radiation within the organs and the radioactive decay behavior of the radionuclide. In various implementations, the radiation dosage to each organ can be determined without performing one or more SPECT-CT scans after the radionuclide is administered. Accordingly, personalized dosimetry can be performed on the patient without the significant costs and burdens associated with ongoing SPECT-CT monitoring.

In various examples, the detectors are configured to generate data that provides quantitative information of the radiation distribution within the organs of the patient. This quantitative information may then be cross-referenced with a CT scan taken shortly before or after therapy administration. Computer simulations can be used to correlate the data gathered with the array of radiation sensors with the organ and tumor-specific activity distribution in the patient's body. Computer simulations of the radiotherapy's presence within the body (e.g., via Monte Carlo simulation tools) can be used to establish the sensitivity matrix between activity in regions of interest in the patient and the customized detector array. Furthermore, if the CT scan shows an organ or a target site for measurement has shifted from the expected position as determined by any earlier scan, and upon which the array of radiation sensor positions was determined, the sensitivity of the array of radiation sensors can still be relied upon once the measurement region is steered by the CT scan taken around the same time. Further, the CT scan maybe performed the same day as the radiotherapy administration, and then measurement with the array of radiation sensors can be done afterward over the period of hours or days necessary to monitor the effectiveness of the treatment by observing uptake and washout.

By removing the need for a quantitative SPECT-CT scan, the patient is free to travel outside of the proximity of a clinical center capable of performing quantitative SPECT-CT imaging after the radionuclide is administered. For instance, the patient may return home, even if they live a significant distance from a hospital that has a SPECT-CT scanner. Although some implementations described herein include performing one or more additional CT scans on the patient after the radionuclide is administered, non-quantitative CT imaging is often available at a wider variety of facilities than SPECT-CT imaging. Thus, various implementations described herein enable patients from areas without facilities capable of conducting quantitative SPECT-CT imaging to participate in personalized dosimetry and to return home sooner than if they were monitored using traditional SPECT-CT means. In addition, various implementations described herein further reduce the cost for monitoring of therapy because CT imaging is less expensive than quantitative SPECT-CT imaging.

Various implementations of the present disclosure will be described in detail with reference to the drawings, wherein like reference numerals present like parts and assemblies throughout the several views. Additionally, any samples set forth in this specification are not intended to be limiting and merely demonstrate some of the many possible implementations.

FIG. 1 illustrates an environment 100 for optimizing detector positions to perform personalized dosimetry. In some implementations, the environment 100 is located in a clinical setting, such as a hospital. In various cases, a patient 102 may have been diagnosed with a type of cancer that is potentially treatable by a radiotherapy. The patient 102 may be a human subject or individual. As used herein, the terms "radiotherapy," "radiation therapy," and their equivalents, may refer to a medical treatment where ionizing radiation is used to kill pathologic cells. In various examples, radiotherapy is used to kill cancer cells within the body of a patient.

Radionuclide therapy is a type of radiotherapy in which a radionuclide is used to deliver the ionizing radiation to the pathologic cells. As used herein, the terms "radionuclide," "radioisotope," and their equivalents, may refer to a molecule, complex, or structure that emits ionizing radiation.

Examples of radionuclides include, for instance, $^{177}$Lu, $^{68}$Ga, $^{225}$Ac, $^{203}$Bi, $^{141}$Ce, $^{159}$Dy, $^{145}$Eu, $^{59}$Fe, $^{67}$Ge, $^{175}$Hf, $^{124}$I, $^{125}$I, $^{126}$I, $^{131}$I, $^{166}$Ho, $^{42}$K, $^{177}$Lu, $^{99}$Mo, $^{13}$N, $^{15}$O, $^{234}$Pa, $^{82}$Rb, $^{72}$Se, $^{119}$Te, $^{231}$U, $^{48}$V, $^{178}$W, $^{125}$Xe, $^{93}$Y, $^{90}$Y, and $^{97}$Zr.

In various cases, a radionuclide is included in a radiopharmaceutical. As used herein, the term "radiopharmaceutical," and its equivalents, refers to a combination of a radionuclide and a binding domain that specifically binds to a receptor. The radionuclide may be attached to the binding domain via a chelator.

In particular implementations, the binding domain of the radiopharmaceutical includes an antibody, an antibody binding fragment, a peptide, a peptide aptamer, one or more nucleic acids, one or more nucleic acid aptamers, one or more spiegelmers, or combinations thereof. "Antibodies" are one example of binding domains and include whole antibodies or binding fragments of an antibody, e.g., Fv, Fab, Fab', F(ab')2, Fc, and single chain Fv fragments (scFvs) or any other effective binding fragments of an immunoglobulin. Antibodies or antigen binding fragments include all or a portion of polyclonal antibodies, monoclonal antibodies, human antibodies, humanized antibodies, synthetic antibodies, chimeric antibodies, bispecific antibodies, mini bodies, and linear antibodies.

Peptide aptamers include a peptide loop (which is specific for a target protein) attached at both ends to a protein scaffold. This double structural constraint greatly increases the binding affinity of the peptide aptamer to levels comparable to an antibody. The variable loop length is typically 8 to 20 amino acids (e.g., 8 to 12 amino acids), and the scaffold may be any protein which is stable, soluble, small, and non-toxic. Peptide aptamer selection can be made using different systems, such as the yeast two-hybrid system (e.g., Gal4 yeast-two-hybrid system) or the LexA interaction trap system.

Nucleic acid aptamers are single-stranded nucleic acid (DNA or RNA) ligands that function by folding into a specific globular structure that dictates binding to target proteins or other molecules with high affinity and specificity, as described by Osborne et al., Curr. Opin. Chem. Biol. 1:5-9, 1997; and Cerchia et al., FEBS Letters 528:12-16, 2002. In particular embodiments, aptamers are small (15 KD; or between 15-80 nucleotides or between 20-50 nucleotides). Aptamers are generally isolated from libraries consisting of 1014-1015 random oligonucleotide sequences by a procedure termed SELEX (systematic evolution of ligands by exponential enrichment; see, for example, Tuerk et al., Science, 249:505-510, 1990; Green et al., Methods Enzymology. 75-86, 1991; and Gold et al., Annu. Rev. Biochem., 64: 763-797, 1995).

As used herein, the term "specifically binds" refers to an association of a binding domain to its cognate binding molecule (e.g., a receptor) with an affinity or $K_a$ (i.e., an equilibrium association constant of a particular binding interaction with units of 1/M) equal to or greater than a threshold, such as $10^5$ M$^{-1}$, while not significantly associating with any other molecules or components in a relevant environment sample. A variety of assays are known for detecting binding domains that specifically bind a particular cognate binding molecule as well as determining binding affinities, such as Western blot, ELISA, and BIACORE® (Cytiva Sweden) analysis (see also, e.g., Scatchard, et al., 1949, Ann. N.Y. Acad. Sci. 51:660; and U.S. Pat. Nos. 5,283,173, 5,468,614, or the equivalent).

Unless otherwise indicated, the practice of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

In various implementations, the binding domain of the radiopharmaceutical specifically binds to a receptor expressed by cancer cells. In various implementations, the receptor is an antigen expressed on a surface of cancer cells. Peptide receptor radionuclide therapy (PRRT) is a type of radionuclide therapy in which the binding domain of the radiopharmaceutical specifically binds to peptide receptors, which are overexpressed by cancer cells compared to non-cancerous cells. For example, the radiopharmaceutical specifically binds to somatostatin receptors (SSRs) expressed by cancer cells. In various cases, the binding domain of a PRRT radiopharmaceutical includes a molecule that mimics somatostatin, such as octreotide, edotreotide, or octreotate. In some implementations, the PRRT radiopharmaceutical further includes dodecane tetraacetic acid (DOTA) as a chelator to attach the radionuclide to the binding domain. Examples of cancers that may be susceptible to treatment by PRRT and other types of radionuclide therapies include neuroendocrine tumors (NETs), thyroid cancers, liver tumors, bone cancers, and the like. Other examples of receptors include prostate-specific membrane antigen (PSMA) receptors, which are expressed in prostate cancer cells. These receptors specifically bind to radiopharmaceuticals such as $^{68}$Ga-PSMA and $^{177}$Lu-PSMA. In addition, thyroid cells uptake iodine, such that thyroid cancers can be targeted by radionuclides like $^{131}$I or $^{124}$I.

Because the binding domain of the radiopharmaceutical specifically binds to the receptor on the cancer cells, the radiopharmaceutical may provide targeted radiation therapy to the cancer cells. However, if the cancer cells of the patient 102 do not express the receptor, then administering the radiopharmaceutical could expose the patient 102 to unnecessary radiation without specifically targeting the cancer cells of the patient 102. Thus, before administering the radiopharmaceutical to the patient 102, a care provider 104 may confirm that the cancer cells of the patient 102 express the receptor targeted by the radiopharmaceutical. The care provider 104, for example, may be a physician (e.g., a radiation oncologist), a medical physicist, or some other type of medical provider that is trained to administer radiotherapy.

To determine whether the cancer cells of the patient 102 express the receptor, an imaging scan may be performed on the patient 102. For example, the environment 100 includes a scanner 106 configured to perform imaging of a patient 104. In some implementations, the scanner 106 is configured to perform PET imaging on the patient 104. In various cases, a radiotracer is administered to the patient 104. As used herein, the terms "radiotracer," "radiolabel," and their equivalents, may refer to a combination of an isotope and a binding domain that specifically binds a receptor, wherein the radiation emitted from the radionuclide is detectable via imaging. The radiotracer may further include a chelator that binds the isotope and the binding domain. According to various examples, the receptor of the radiotracer is the same receptor that is specifically bound by the binding domain of the radiopharmaceutical.

In various implementations, the PET radiotracer includes a positron-emitting isotope, such as $^{11}$C, $^{13}$N, $^{15}$O, $^{18}$F, $^{68}$Ga, $^{61}$Cu, $^{64}$Cu, $^{89}$Zr, $^{86}$Y, $^{52}$Mn, $^{55}$CO, $^{89}$Ze, or $^{82}$Rb. As the nucleus of the isotope emits a positron, the positron collides with an electron in nearby tissue. Two photons (e.g., annihilation photons) are emitted as a result of the collision of the positron and the electron. The scanner 106 may include sensors (e.g., gamma detectors) configured to detect the photons emitted from the isotope of the radiotracer. Based on the detected photons, the scanner 106 may determine the distribution of the isotope within the body of the patient 104 by generating a three-dimensional (3D) image of the patient 104 representative of the distribution of the radiotracer in the body of the patient 104 (also referred to as a "PET scan"). If the radiotracer is bound to discrete tumors within the patient 104, then the scanner 106 may determine the location of those tumors based on the detected photons. Accordingly, the PET scan may confirm that the cancer cells of the patient 104 express the receptor for the radiotherapy.

In various implementations, the scanner 106 includes a CT scanner configured to obtain a CT scan of the patient 104. According to some cases, the scanner 106 is a PET-CT scanner configured to perform both PET and CT imaging on the patient 102. For instance, the scanner 106 may include at least one x-ray emitter configured to emit x-rays through the patient 104. Anatomical structures within the patient 102, such as bones, organs, and other tissues, may differentially attenuate the x-rays. The scanner 106 may further include detectors configured to detect x-rays that have passed through the patient 104. In various implementations, the scanner 106 emits and detects the x-rays at various angles, such that the scanner 106 is configured to construct tomographic images of the internal anatomy of the patient 104. Further, the scanner 106 may construct a three-dimensional (3D) image (also referred to as a "CT scan") of the patient 104 based on the tomographic images. If the scanner 106 is a PET-CT scanner, the scanner 106 may overlay the distribution of the radiotracer on the CT scan of the patient 104, which can provide enhanced localization of the radiotracer (and corresponding tumor sites) with respect to other anatomical structures of the patient 102 visible on the CT scan.

The scanner 106 may output imaging data 108 representative of the photons detected by the scanner 106 to a computing device 110. For example, the imaging data 108 may be representative of the gamma rays and/or x-rays detected by the detectors in the scanner 106, of the PET scan of the patient 102, of the CT scan of the patient 102, of the PET-CT scan of the patient 102, or any combination thereof. In various implementations, the imaging data 108 represents digital data. For example, if the imaging data 108 is indicative of the gamma rays and/or x-rays detected by the detectors of the scanner 106, then the scanner 106 may convert the analog signals detected by the detectors into digital signals that are packaged into the imaging data 108. According to some cases, the imaging data 108 includes one or more data packets (e.g., Internet Protocol (IP) data packets) and/or datagrams (e.g., TCP datagrams). The scanner 106 may transmit the imaging data 108 over one or more communication interfaces connected to the computing device 110. For example, the scanner 106 may transmit the imaging data 108 over at least one wired interface (e.g., an electrical cord, an optical interface, etc.) between the scanner 106 and the computing device 110. In some cases, the scanner 106 may transmit the imaging data 108 over at least one wireless interface (e.g., a $3^{rd}$ Generation Partnership Project (3GPP) interface, such as a Long Term Evolution (LTE) wireless interface or a New Radio (NR) wireless interface; an Institute of Electrical and Electronics Engineers (IEEE) interface, such as a BLUETOOTH® interface or a WI-FI® interface; etc.) between the scanner 106 and the computing device 110.

In various implementations, the computing device 110 may output an image of the patient 102 to the care provider 104. In some cases, the computing device 110 constructs the image based on the imaging data 108 and/or outputs an image constructed by the scanner 106 that is indicated in the imaging data 108. In various examples, the computing device 110 includes a display that visually outputs the image. For instance, the computing device 110 displays the CT scan, the PET scan, the PET-CT scan, or a combination thereof, to the care provider 104. Accordingly, the care provider 104 may determine whether the cancer cells of the patient 102 express the receptor for the radiopharmaceutical.

In general, the radiopharmaceutical may be administered to the patient 102 in a limited number of doses. According to various implementations, the patient 102 may receive each dose of the radiopharmaceutical by ingestion or injection (e.g., intravenous (IV) injection). After administration, the radiopharmaceutical may specifically bind to the receptor on the cancer cells of the patient 102 and may output radiation to those cancer cells. In various cases, the radiation differentially kills the cancer cells within the patient 102. However, the radiation from the radiopharmaceutical is not output solely to the cancer cells of the patient 102. The radiation from the radiopharmaceutical may damage noncancerous cells of the patient 102.

In particular implementations, the body of the patient 102 removes circulating radiopharmaceutical. This process is known as "washout." As a result, the radiopharmaceutical may accumulate in organs associated with removing the radiopharmaceutical from the body. At some point, the amount of radiopharmaceutical administered to the patient 102 could cause inordinate damage to these organs. Thus, the amount of radiation tolerated by these organs can be an important limit to safe dosages of the radiopharmaceutical. These organs may be referred to herein as "dose-limiting organs." Examples of dose-limiting organs include one or more kidneys, a liver, a spleen, and bone marrow.

Conventionally, a radiopharmaceutical is administered in the same number of doses to all patients in order to avoid excessive radiation to the dose-limiting organs. However, different patients may exhibit different uptake and washout kinetics to the same amount of radiotherapy. For example, the same dose of a radiopharmaceutical may produce different radiation dosages to the kidneys of different patients. In particular, by administering patients with the same number of radiopharmaceutical doses, some patients may tolerate additional doses that could provide them with enhanced cancer treatment.

In various implementations, a garment 112 configured to monitor radiation dosages of the dose-limiting organs of the patient 102 after administration of the radiotherapy is customized for the patient 102. The garment 112 may be worn by the patient 102 as the scanner 106 is imaging the patient 102. In particular cases, the patient 102 may be lying down while wearing the garment 112 and being imaged by the scanner 106. In various cases, the garment 112 may include a wrap that is at least partially disposed around the torso of the patient 102. The wrap may include a fabric or some other type of flexible material. In some examples, the garment 112 further includes a shell. The shell may include a solid material (e.g., polystyrene foam, STYROFOAM® (Dow Chemical Co., Midland, MI), silicon, fiberglass, etc.) with a surface that is molded and/or contoured around an external surface of the patient 102. In some cases, the shell includes a continuous structure disposed between the patient 102 and the bed of the scanner 106, or multiple panels integrated with the garment 112. According to some examples, the garment 112 includes a vest that is fastened around the torso of the patient 102.

The garment 112 may further include fiducial markers 114. The fiducial markers 114 may include a material that attenuates x-rays or is otherwise visible on the CT scan of the patient 102. In some implementations, the fiducial makers 114 include a metal and/or a polymer. According to some examples, the fiducial markers 114 include a pattern (e.g., a lattice) distributed across the garment 112 and/or discrete shapes distributed across the garment 112.

The fiducial markers 114 of the garment 112 may be visible on the CT scan of the patient 102 that is generated by the scanner 106. In various cases, the scanner 106 and/or the computing device 110 may be configured to select optimal positions along the garment 112 for detecting radiation dosages to the dose-limiting organs. For example, depictions of the dose-limiting organs may be segmented in the CT scan and/or the PET-CT scan. In some cases, the care provider 104 may manually segment the dose-limiting organs depicted in the CT scan and/or the PET-CT scan. In various examples, the dose-limiting organs may be automatically segmented by the scanner 106 and/or computing device 110. Automatic segmentation can be performed using classical computer vision techniques and/or machine learning. Examples of segmentation techniques include thresholding (e.g., Otsu's method, balanced histogram thresholding, etc.), k-means clustering, edge detection, curve propagation, Markov random fields, U-net-based segmentation, and so on. The scanner 106 and/or the computing device 110 may store one or more computing models that, when executed by a processor (e.g., a graphics processing unit (GPU)), segment the imaging data 108 and generate data indicating the locations of boundaries of the organs of the patient 102. Thus, the locations of the dose-limiting organs may be determined based on the image(s) captured by the scanner 106.

In addition, a set of potential positions may be defined along the garment 112 with respect to the fiducial markers 114. For each of the potential positions, the scanner 106 and/or the computing device 110 may determine a sensitivity of the position to the location of at least one of the dose-limiting organs. Further, the scanner 106 and/or the computing device 110 may determine a sensitivity of the position to the location of at least one of the tumor sites indicated in the PET scan and/or PET-CT. In some cases, the scanner 106 and/or computing device selects a set of the potential positions with the highest sensitivity to the location of at least one of the dose-limiting organs and/or the lowest sensitivity to the location of at least one of the tumor sites. In particular implementations, a predetermined number of potential positions are selected, such as 10 to 15 positions along the garment 112. The selected positions may be defined as optimal positions for estimating the radiation dosages to the dose-limiting organs. In various implementations, the computing device 110 outputs the selected positions to the care provider 104.

In various cases, the garment 112 may be subsequently customized by placing a discrete set of detectors at the selected positions along the garment 112. For example, the detectors may be glued, sewed, or otherwise attached to the selected positions. The detectors may be configured to detect photons. The customized garment 112 may be provided to the patient 102 when the patient 102 is dosed with the radiopharmaceutical. At regular intervals after receiving the dose of the radiopharmaceutical, the patient 102 may be directed to wear the garment 112 (e.g., while lying down). The detectors in the garment 112 may detect photons emitted by the radionuclide within the radiopharmaceutical. Based on the photons detected by the detectors, the positions of the detectors in the garment 112, and the locations of the dose-limiting organs of the patient 102, the radiation dosages to the dose-limiting organs can be derived. The computing device 110 may output indications of the radiation dosages to the care provider 104. Accordingly, it may be determined (e.g., the care provider may then decide) whether the patient 102 can tolerate additional radiopharmaceutical doses. For instance, the care provider 104 and/or the computing device 110 may compare the radiation dosage to a dose-limiting organ of the patient 102 to a threshold associated with a maximum radiation dosage to that dose-limiting organ.

Figure 2:
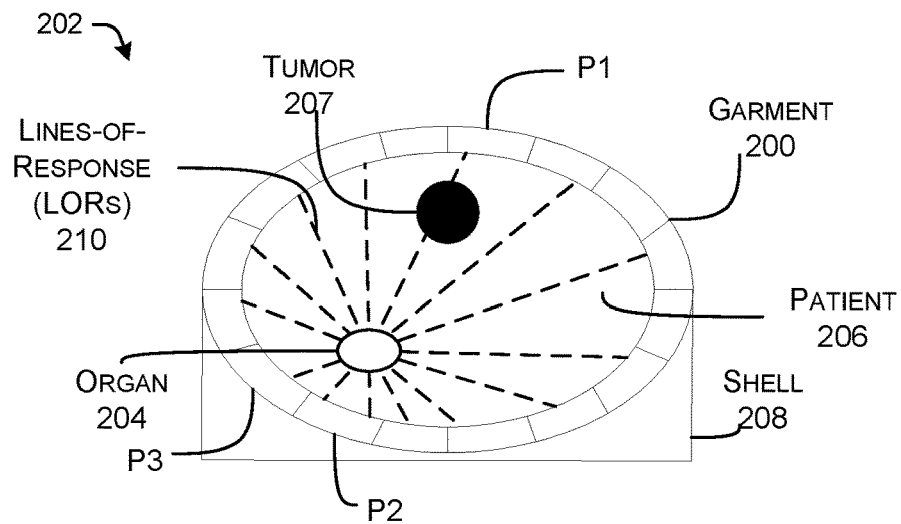
FIG. 2 illustrates a diagram for determining optimized positions for the detectors based on the location of an organ.
Figure 3:
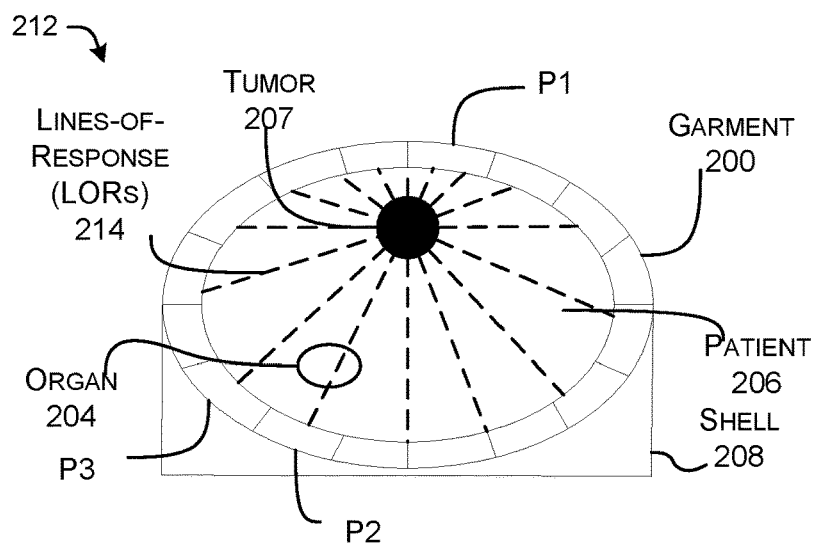
FIG. 3 illustrates a diagram for determining optimized positions for the detectors based on the location of the tumor.

FIGS. 2 and 3 illustrate diagrams for determining optimized placement of detectors in a garment 200 based on sensitivity. FIG. 2 illustrates a diagram 202 for determining optimized positions for the detectors based on the location of an organ 204. The diagram 202 illustrated in FIG. 2 represents a two-dimensional (2D), cross-sectional image of a patient 206 wearing the garment 200. The patient 206 may further include a tumor 207 that is visible in the diagram 202. The garment 200 and patient 206, for example, may be the garment 112 and patient 102 described above with respect to FIG. 1. Furthermore, the diagram 202 may be derived from a PET-CT scan generated by the scanner 106 described above with reference to FIG. 1.

The garment 200 may include a shell 208. The shell 208 includes a solid material that may be contoured around a surface of the patient 206. In some cases, the shell 208 is at least partially molded around the patient 206. In the implementation illustrated in FIG. 2, the patient 206 is lying down and resting on the shell 208, which may support the weight of the patient 206 during imaging. According to some cases, the shell 208 may reliably stabilize the patient 206 to prevent movement during scanning. Furthermore, the shell 208 may be used to reliably align the position of the patient 206 with the garment 200 during image acquisition and detection data acquisition. The shell 208 may be disposed at an external surface of the garment 200, or may be disposed inside of at least one layer of the garment 200 (e.g., disposed within a fabric pocket of the garment 200). In some cases, the shell may be comprised of multiple pieces and fully encircle the patient.

Various positions may be defined along the garment 200. As illustrated in FIG. 2, the positions are disposed radially around the patient 206. For example, the positions include a first position P1, a second position P2, and a third position P3. Other positions, besides the first to third positions P1 to P3 may be additionally defined along the garment 200.

In various implementations, one or more optimal positions along the garment 200 for detecting photons from the organ 204 are determined based on the location of the organ 204. In some implementations, a depiction of the organ 204 is segmented in the scan. For instance, the depiction of an outer boundary of the organ 204 in the image is defined within the patient 206 in order to define the location of the organ 204. The organ 204 may be manually segmented by a user and/or automatically segmented by a computer.

The sensitivity of each possible position along the garment 200 to photons emitted from the organ 204 may be determined. For example, FIG. 2 illustrates several lines-of-response (LORs) 210 radiating from the organ 204. The LORs 210 are evenly spaced from one another in terms of angle, and represent possible directions that photons from the organ 204 could be emitted. When the patient 206 is dosed with a radiopharmaceutical that is disposed in the organ 204, photons from the radionuclide of the radiopharmaceutical may be emitted in any direction with equal likelihood. Therefore, the density of LORs 210 in a given region illustrated in the diagram 202 may correspond to the likelihood that photons from the organ 204 will cross the region during radiotherapy treatment. In particular, the density of LORs 210 intersecting each position along the garment 200 is related to the likelihood that the photons from the organ 204 will also intersect that position. Thus, a position intersecting a greater number of LORs 210 is more likely to receive a greater number of photons from the organ 204 than a position intersecting a fewer number of the LORs 210. The position receiving the greater number of photons may be a more optimal position for detecting the photons than the position receiving the fewer number of photons. In the example of FIGS. 2, P2 and P3 may be superior positions to P1, because P2 and P3 each intersect two LORs 210 and P1 only intersects a single LOR 210.

In general, positions near the locations of the organ 204 may be more likely to receive photons from the organ 204 due not only to the density of the LORs 210, but also due to attenuation (i.e., absorption and/or scattering) of photons along the paths between the positions and the organ 204. For example, a path between the organ 204 and P2 is shorter than the path between the organ 204 and P1. The longer path between the organ 204 and P1 through the patient 206 is more likely to include a structure that will attenuate photons from the organ 204 than the shorter path between the organ 204 and P2. For instance, calcification in the tumor 207 may scatter photons emitted from the organ 204 towards P1. For this additional reason, P1 is more likely to receive fewer photons from the organ 204 than P2.

FIG. 3 illustrates a diagram 212 for determining optimized positions for the detectors based on the location of the tumor 207. In various implementations, the optimized positions may be further determined based on the sensitivity of each of the positions along the garment 200 with respect to the tumor 207. For example, positions with less sensitivity to the tumor 207 may be preferred over positions with greater sensitivity.

According to some cases, the location of the tumor 207 may be determined. For example, a depiction of the tumor 207 may be manually segmented in a scan (e.g., an image) by a user and/or automatically segmented by a computer. In addition, LORs 214 from the tumor 207 may be defined based on the determined location of the tumor 207. Positions on the garment 200 that intersect a greater number and/or density of LORs 214 may be defined as having greater sensitivity to the tumor 207, and positions on the garment 200 that intersect a lower number and/or density of LORs 214 may be defined as having a lower sensitivity to the tumor 207. However, for the purpose of detecting radiation from the organ 204, rather than the tumor, the positions with lower sensitivity to the tumor 207 may be preferred over positions with higher sensitivity to the tumor 207. Thus, based on the location of the tumor 207, P2 and P3 (each of which intersect single LORs 214) may be preferred positions over P1 (which intersects multiple LORs 214).

Although FIGS. 2 to 3 are described with respect to 2D cross-sections of the garment 200 and patient 206, implementations are not so limited. The sensitivities of different positions along the garment 200 can be determined three-dimensionally, in various implementations.

Figure 4:
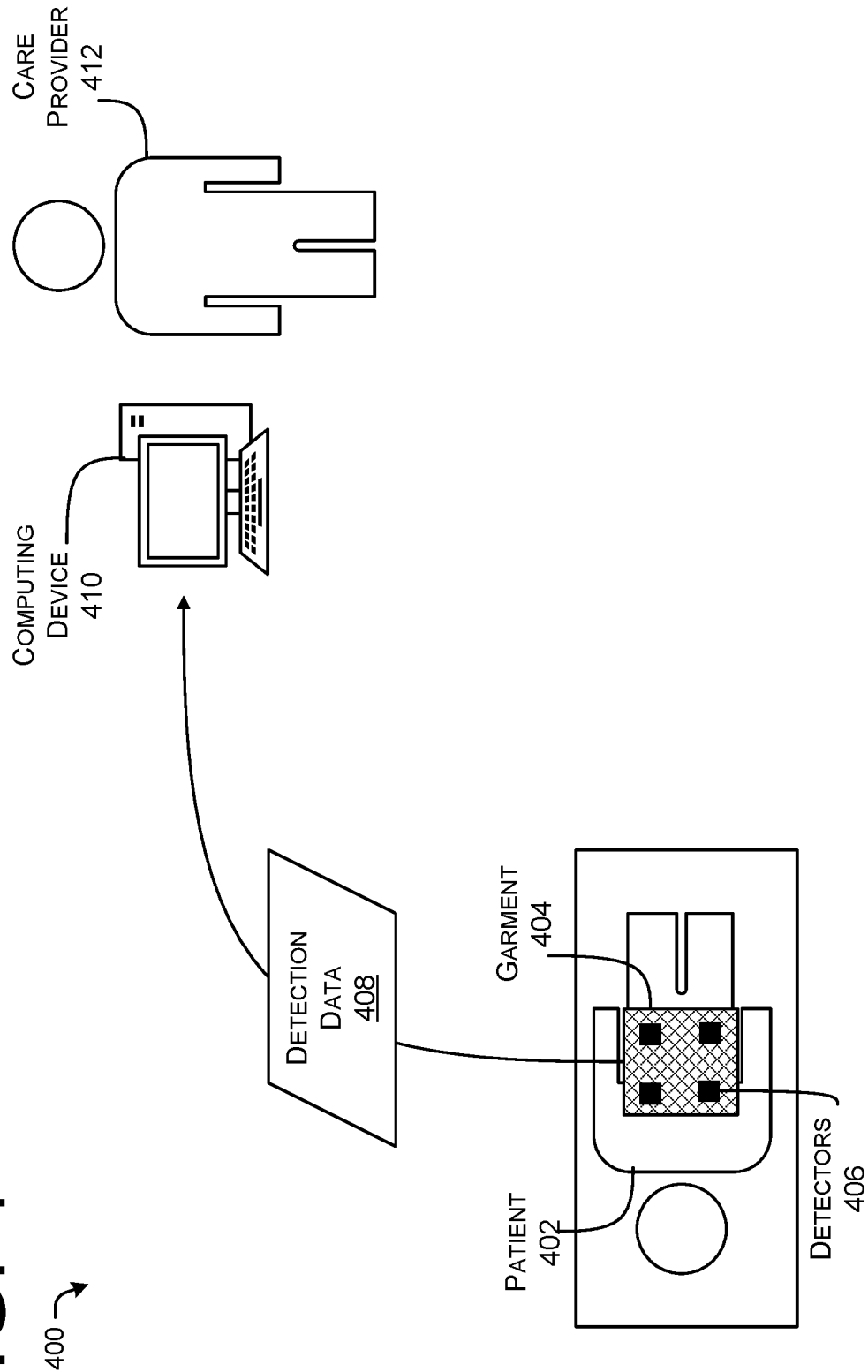
FIG. 4 illustrates an example environment for determining radiation dosages to one or more dose-limiting organs.

FIG. 4 illustrates an example environment 400 for determining radiation dosages to one or more dose-limiting organs. As shown, the environment 400 includes a patient 402 who is wearing a garment 404. In some cases, the patient 402 is located remotely from a care facility, such as remotely from a hospital. The patient 402, for example, may be located at home.

In various implementations, the patient 402 has been administered a radiopharmaceutical. For example, the patient 402 has received at least one dose of the radiopharmaceutical by being injected with the radiopharmaceutical. In various implementations, the radiopharmaceutical includes a binding domain that specifically binds to a receptor expressed on cancer cells of the patient 402. The radiopharmaceutical may further include a radionuclide that emits ionizing radiation in the form of beta particles and/or photons. The radiation released by the radiotherapy may kill the cancer cells. However, the radiopharmaceutical may also wash out into one or more dose-limiting organs of the patient 402, such as a kidney, a liver, a spleen, or a bone marrow of the patient 402.

The amount of radiation exposed to the dose-limiting organs of the patient 402 can be determined using the garment 404. In various implementations, the garment 404 includes multiple detectors 406. For instance, the garment 404 may include 1 to 100, 5 to 50, or 10 to 15 detectors 406. The detectors 406 are placed at positions along the garment 404 that are optimized for detecting photons from the dose-limiting organs of the patient 402. For example, the positions of the detectors 406 are previously determined based on a CT scan and/or a PET-CT scan of the patient 402 prior to administration of the radiotherapy.

In various implementations, the patient 402 is lying down while wearing the garment 404. According to some instances, the positions of the detectors 406 were selected based on a scan (e.g., the CT and/or PET-CT scan) performed while the patient 402 was lying down. Thus, the positions of the detectors 406 relative to the dose-limiting organs may be predetermined while the patient 402 is lying down.

During an acquisition period, the detectors 406 may detect photons from the patient 402. The acquisition period may be a time period that extends for no longer than 1 minute, 5 minutes, 30 minutes, 1 hour, or 10 hours. For example, the acquisition period may last for 10 minutes to 1 hour. In various implementations, each one of the detectors 406 may determine a number of photons received by the detector 406 during the acquisition period (also referred to as a "photon count"). The garment 404 may generate detection data 408 based on the photons detected by the detectors 406. For example, the detection data 408 may indicate the photon counts detected by each of the respective detectors 406 integrated into the garment 404 during the acquisition period. In some implementations, the detection data 408 may further indicate identifiers of the detectors 406. In some cases, the positions of the detectors 406 along the garment 404 are stored by the garment 404 and reported in the detection data 408.

In various implementations, the garment 404 includes a processor configured to generate the detection data 408. The detectors 406 may be configured to generate analog electrical signals indicative of the detected photons. In some cases, the garment 404 includes one or more analog-to-digital converters (ADCs) configured to convert the analog electrical signals into one or more digital signals that are provided to the processor. The processor may generate the detection data 408 based on the digital signal(s). In addition, the garment 404 may include memory configured to store data associated with the patient 402, the garment 404, the detectors 406, or a combination thereof. For example, the memory may store a name or patient identifier of the patient 402; an identifier of the garment 404, identifiers of the detectors 406 and/or positions of the detectors 406 along the garment 404; and so on. The processor in the garment 404 may generate the detection data 408 to indicate any of the information stored in the memory. Accordingly, the detection data 408 may identify the patient 402 and/or garment 404 associated with the detection data 408.

The garment 404 may transmit the detection data 408 to a computing device 410. In various implementations, the garment 404 includes a transmitter (e.g., a transceiver) configured to transmit the detection data 408 from the garment 404. In some cases, the transmitter transmits the detection data 408 to a mobile device (not illustrated), such as a mobile phone 402, which may transmit the detection data 408 to the computing device 410. The transmitter may, in some cases, transmit the detection data 408 wirelessly over one or more communication networks. In some cases, a wired interface connects the garment 404 to the mobile device or to the computing device 410. The detection data 408 may be transmitted to the computing device 410 in a wireless and/or wired manner.

In various implementations, the garment 404 may include an input device communicatively coupled to the processor and configured to receive an input signal from a user. For example, the garment 404 may include a touch screen and/or button configured to detect a touch signal from the user, a microphone configured to detect an audible signal from the user, or the like. The processor may cause the garment 404 to begin and/or end the acquisition time based on the input signal. For instance, the processor may activate the detectors 406 and/or deactivate the detectors 406 based on the input signal. In a specific example, the patient 402 may press a button that triggers the beginning of the acquisition time for the detectors 406 and may press the button that triggers the end of the acquisition time.

In addition, the garment 404 may include a power source configured to supply electrical power to the detectors 406, the ADCs, the processor, the memory, the transmitter, the input device, or any combination thereof. For instance, the garment 404 may include one or more batteries (e.g., Lithium ion batteries). In some cases, the power source can be recharged by plugging the garment 404 into wall current. However, in various implementations, the garment 404 can detect the photons from the dose-limiting organs and provide the detection data 408 without being plugged in to the wall current.

The computing device 410 may be located remotely from the patient 402 and the garment 404. For instance, the computing device 410 may be located on the premises of a hospital. In various implementations, the computing device 410 may be configured to determine radiation dosages to the respective organs-of-interest of the patient 402 based on the detection data 408. The computing device 410 may identify the amount of photons detected by the detectors 406 based on the detection data 408. Furthermore, the computing device 410 may identify the relative locations of the organs-of-interest with respect to the positions of the detectors 406. In some cases, the computing device 410 may determine these relative locations based at least in part on the detection data 408. Based on the amount of photons detected by the detectors 406 and the relative locations of the organs-of-interest with respect to the detectors 406, the computing device 410 may determine amount of photons emitted from each of the organs-of-interest during the acquisition period.

According to various implementations, the patient 402 may wear the garment 404 during multiple acquisition periods during the same radiopharmaceutical dosage. For example, the patient 402 may be instructed to wear the garment 404 once every 24 hours for several days after receiving the dose of the radiopharmaceutical. Each acquisition period may extend for 5 minutes to one hour, in some implementations. In some cases, the detection data 408 indicates the photons detected by the detectors 406 during multiple acquisition periods. In particular implementations, the garment 404 generates new detection data 408 for each acquisition period.

In some cases, the patient 402 may receive multiple doses of the radiopharmaceutical. For example, the patient 402 may receive a first dose of the radiopharmaceutical at a first time, and a second dose of the radiopharmaceutical at a second time. The garment 404 may detect photons from the dose-limiting organs of the patient 402 in one or more acquisition times subsequent to each dose of the radiopharmaceutical. In various implementations, the garment 404 may transmit one or more instances of detection data 408 indicating the photons detected by the detectors 406 during acquisition periods associated with multiple doses of the radiopharmaceutical.

According to some examples, the computing device 410 determines an aggregate radiation dosage to each dose-limiting organ. In various implementations, the computing device 410 may identify, store, or determine a half-life or other type characteristic indicative of the radioactive decay of the radionuclide of the radiopharmaceutical over time. Based on the characteristic and the radiation dosage to an example organ during one or more acquisition times, the computing device 410 may determine a total dosage of radiation to the example organ over the course of one or more doses of the radiopharmaceutical that are administered to the patient 402. In various cases, the computing device 410 may calculate an aggregate radiation dosage to an organ by adding different radiation dosages from respective radiopharmaceutical treatments administered to the patient 402.

The computing device 410 may output, to a care provider 412, a report indicating one or more radiation dosages to one or more dose-limiting organs of the patient 402. For example, the computing device 410 may include a display screen that visually presents the report. In some cases, the computing device includes a speaker configured to audibly present the report.

In some implementations, the computing device 410 may further compare the radiation dosages to one or more thresholds. For example, the computing device 410 may determine whether the radiation dosage to a particular organ over one or more radiopharmaceutical treatments administered to the patient 402 has exceeded a threshold. In some cases, the computing device 410 compares the radiation dosages of multiple dose-limiting organs to respective thresholds. In various cases, if the radiation dosages are less than the respective thresholds, then an additional radiopharmaceutical dose may be indicated for the patient 402. For example, the computing device 410 may output (e.g., visually and/or audibly), to the care provider 412, a message indicating that the radiation dosages are less than the respective thresholds for each organ at risk 402.

Figure 5:
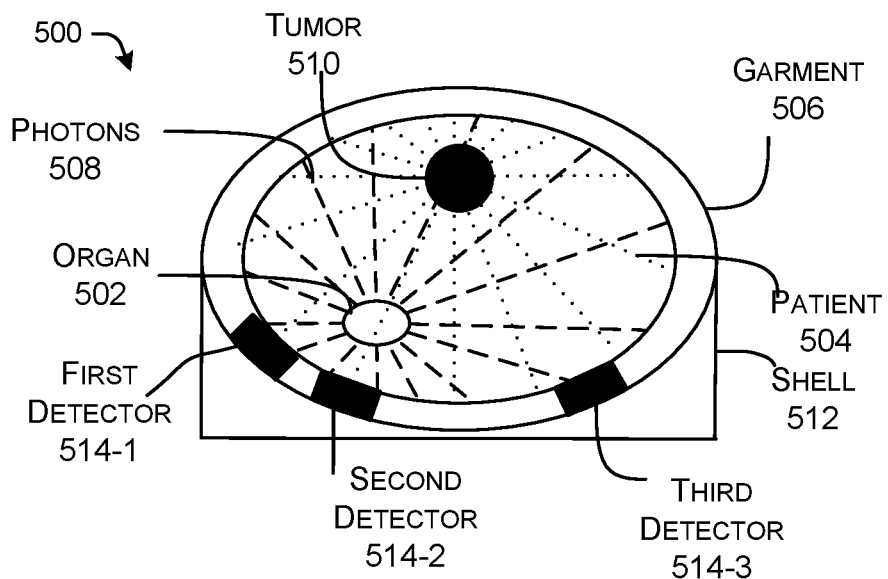
FIG. 5 illustrates a diagram for determining the radiation dosage from an organ of a patient.

FIG. 5 illustrates a diagram 500 for determining the radiation dosage from an organ 502 of a patient 504. In various implementations, the patient 504 is wearing a garment 506. The patient 504 may be lying down while wearing the garment 506. In some examples, the patient 504 is the patient 502 and the garment 506 is the garment 404 described above with reference to FIG. 4.

The garment 506 may include a shell 512. The shell 512 includes a solid material that may be contoured around a surface of the patient 502. In some cases, the shell 512 is at least partially molded around the patient 502. In some cases, the shell fully encircles the patient. In the implementation illustrated in FIG. 5, the patient 502 is lying down and resting on the shell 512, which may support the weight of the patient 502 during photon detection. According to some cases, the shell 512 may reliably stabilize the patient 206 to prevent movement during detection. Furthermore, the shell 512 may be used to reliably align the position of the patient 502 with the garment 506 during image acquisition and detection data acquisition. The shell 512 may be disposed at an external surface of the garment 506, or may be disposed inside of at least one layer of the garment 200 (e.g., disposed within a fabric pocket of the garment 506).

The patient 502 may have been administered a dose of a radiopharmaceutical. Photons 508 from the radiopharmaceutical may be emitted from the organ 502 as well as a tumor 510 within the patient 504. Various detectors integrated into the garment 506, including a first detector 514-1, a second detector 514-2, and a third detector 514-3, may detect the photons 508 from the organ 502 and the tumor 510. For example, each one of the first detector 514-1, the second detector 514-2, and the third detector 514-3 may detect a number of photons that it receives during an acquisition period.

In various implementations, the radiation dosage to the organ 502 by the radiopharmaceutical can be determined based on the photons 508 detected by the first detector 514-1, the second detector 514-2, and the third detector 514-3. In particular examples, the position of the organ 502 relative to the first detector 514-1, the second detector 514-2, and the third detector 514-3 may be known. In addition, the position of the tumor 510 relative to the first detector 514-1, the second detector 514-2, and the third detector 514-3 may be known. For instance, the position of the organ 502 and/or the tumor 510 relative to the first detector 514-1, the second detector 514-2, and the third detector 514-3 may be known based on a CT scan performed on the patient 504 when the patient 504 is wearing the garment 506. For instance, these positions can be determined based on a PET-CT scan performed before the patient 504 is dosed with the radiopharmaceutical or a CT scan performed on the patient 504, which may be performed after the patient 504 has received an initial dose of the radiopharmaceutical.

The photons 508 detected by the first detector 514-1, the second detector 514-2, and the third detector 514-3 may be emitted from the organ 502 and the tumor 510. However, the number of photons received by a detector from a source (e.g., the organ 502 or the tumor 510) may be inversely proportional to the distance between the detector and the source. Further, the geometry of the detector itself may impact the likelihood that each photon it receives is from the organ 502 or the tumor 510. For example, each one of the first detector 514-1, the second detector 514-2, and the third detector 514-3 may be associated with a specific field-of-view (e.g., a cone) that represents the viewing window from which it can receive the photons 508. For example, if the tumor 510 is not within the field-of-view of the third detector 514-3, then the third detector 514-3 may receive negligible (or no) photons 508 from the tumor 510. The relative positions of the first detector 514-1, the second detector 514-2, and the third detector 514-3 to the organ 502, as well as the fields-of-view of the first detector 514-1, the second detector 514-2, and the third detector 514-3 to the organ 502, can be used to determine the sensitivities of the first detector 514-1, the second detector 514-2, and the third detector 514-3 to the organ 502.

In various implementations, the amount of photons detected from the organ 502 can be determined based on the (1) amount of photons detected by the first detector 514-1, the second detector 514-2, and the third detector 514-3 during the acquisition period, and (2) the sensitivities of the first detector 514-1, the second detector 514-2, and the third detector 514-3 to the organ 502. For example, the first detector 514-1 may be more sensitive to the organ 502 than the tumor 510, and thus a higher portion of the photons 508 detected by the first detector 514-1 may be attributed to the organ 502 than the tumor 510. In various implementations, the radiation dosage of the organ 502 may be derived based, at least in part, on the amount of photons detected from the organ 502. In various examples, the dosage to a single organ (e.g., the organ 502) can be derived based on the photon counts from multiple detectors (e.g., the first detector 514-1, second detector 514-2, and third detector 514-3) monitoring the patient 504. The photons 508 detected by the detectors may originate from the organs (e.g., the organ 502), tumors (e.g., tumor 510), and background activity within the anatomy of the patient. The sensitivity of each detector to regions within the body of the patient 504 may be based on the position and/or orientation of the detector. In general, each detector is positioned and oriented such that it has a nonzero sensitivity to multiple regions within the body of the patient 504.

Figure 6:
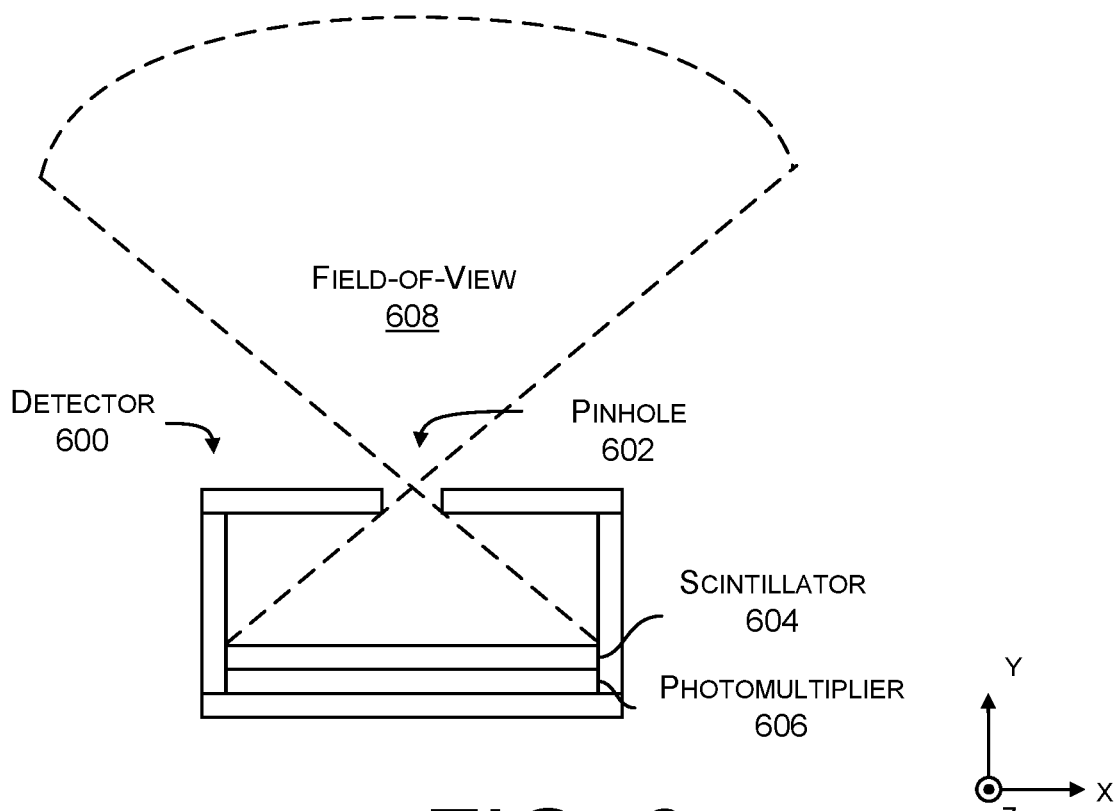
FIG. 6 illustrates an example cross-section of a detector.

FIG. 6 illustrates an example cross-section of a detector 600. In various implementations, the detector 600 includes a sensing face that includes a pinhole 602. The pinhole 602 may be an aperture through which photons can enter the detector 600. Opposite the sensing face of the detector 600 and within an interior space, the detector 600 includes a scintillator 604 disposed on a photomultiplier 606.

In various implementations, the scintillator 604 includes a crystal. The crystal may include an inorganic material, such as cerium-doped gadolinium aluminum gallium garnet (GAGG(Ce)). When the scintillator 604 receives a photon (e.g., emitted by a radionuclide and transmitted through the pinhole 602), the scintillator may absorb the energy of the photon and release the absorbed energy in the form of additional photons (i.e., light photons), wherein the number of additional photons produced is proportional to the amount of energy deposited in the scintillator 604.

The photomultiplier 606 may be configured to convert the additional photons emitted by the scintillator into an electrical signal. In some implementations, the photomultiplier 606 includes a semiconductor, such as silicon. For instance, the photomultiplier 606 may be a silicon photomultiplier (SiPM). In various implementations, the photomultiplier 606 is electrically connected to an ADC and/or a processor (e.g., a time over threshold circuit) configured to generate a digital signal based on the electrical signal output by the photomultiplier 606. The electrical signal output by the photomultiplier 606 and the digital signal may be indicative of energy of the individual photons that are detected by the detector 606.

In various cases, the detector 600 is associated with a field-of-view 608. The field-of-view 608 represents a volume of space from which photons that are detectable by the detector 60 may be transmitted. For example, a radionuclide (e.g., in a radiopharmaceutical) disposed in the field-of-view 608 of the detector 600 may emit a photon that is transmitted through the pinhole 602 and is received by the scintillator 604. The shape of the field-of-view 608 may depend on the geometry of the pinhole 602 and/or the scintillator 604. In examples wherein the pinhole 602 is circular (e.g., along an xz plane), the field-of-view 608 may have a cone shape.

According to various examples, the detector 600 may be placed on a garment in a position that is optimized to detect organs-of-interest. For example, the detector 600 may be positioned such that at least one organ-of-interest may be disposed in the field-of-view 608 of the detector 600. In examples in which multiple detectors 600 are placed on the garment, the detectors 600 may be positioned such that different combinations of tumors and/or organs are disposed in their respective fields-of-view 608, such that it may be possible to mathematically identify the fraction of the total number of photons detected from different volumes within the patient and/or distinguish between detected photons transmitted from different locations, such as different organs. In some implementations, the pinhole 602 of the detector 600 is optimized for a field-of-view 608 that includes one or more target organs and/or excludes one or more tumors. For example, the detector 600 may have a relatively small pinhole 602 to produce a relatively narrow field-of-view 608, or may have a relatively large pinhole 602 to produce a relatively wide field-of-view 608.

Figure 7:
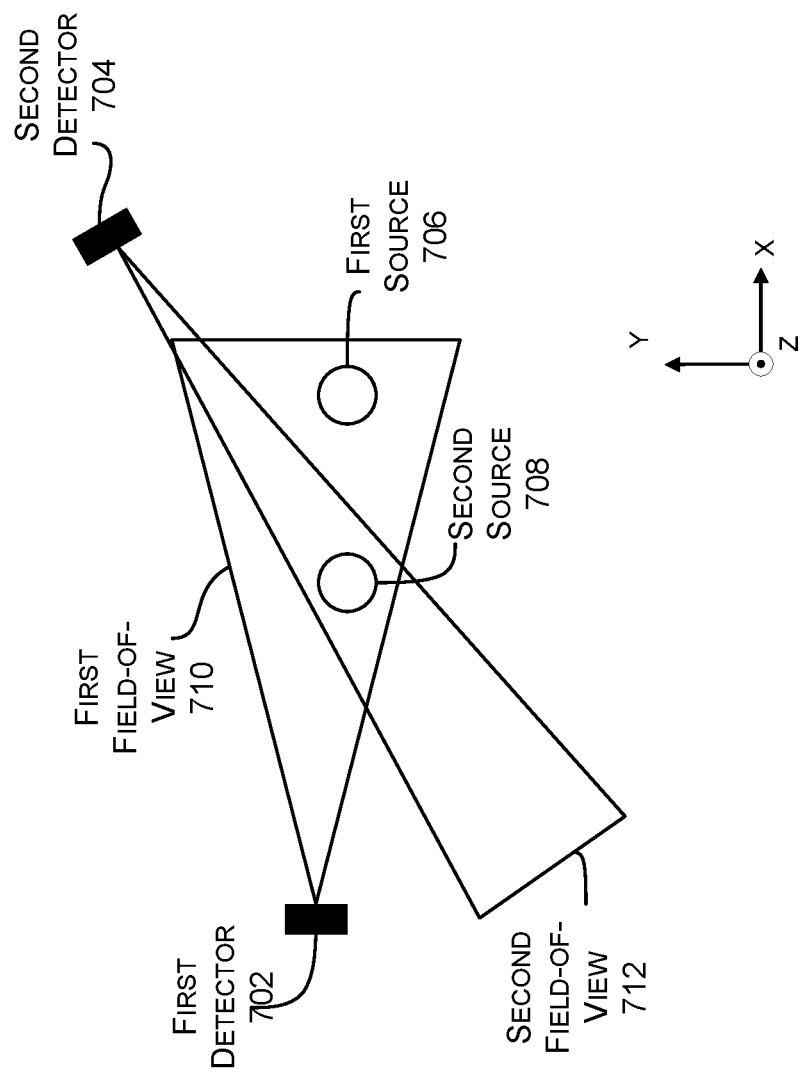
FIG. 7 illustrates an example environment in which multiple detectors can be used to determine radiation dosages to different organs of a patient.

FIG. 7 illustrates an example environment 700 in which multiple detectors can be used to determine radiation dosages to different organs of a patient. The environment 700 includes a first detector 702 and a second detector 704. In various implementations, the first detector 702 and the second detector 704 may be disposed on and/or in a garment that is worn by a subject (e.g., a patient).

In addition, the environment 700 includes a first source 706 and a second source 708. The first source 706 and the second source 708 may be regions within the subject where a radiopharmaceutical accumulates within the body of the subject. For example, the first source 706 and the second source 708 may be organs, tumors, or the like. In various implementations, the locations of the first source 706 and the second source 708 are known based on an anatomic scan of the subject. For example, the locations of the first source 706 and the second source 708 may be determined based on a CT scan of the subject and/or a PET-CT scan of the subject.

The first detector 702 may have an associated first field-of-view 710. In addition, the second detector 704 may have a second field-of-view 712. In various implementations, the first field-of-view 710 and the second field-of-view 712 are positioned based on the locations of the first source 706 and the second source 708. For example, to distinguish between photons transmitted by the first source 706 and the second source 708, the first field of view 710 may be oriented to include the first source 706 and the second source 708, whereas the second field-of-view 712 may be oriented to include the second source 708 without including the first source 706. Other configurations of the first field-of-view 710 and the second field-of-view 712 are also possible. For example, the first field-of-view 710 may be oriented to include the first source 706 without the second source 708. In various implementations, the first field-of-view 710 includes a different combination of the first source 706 and the second source 708 than the second field-of-view 712.

In the example of FIG. 7, the first detector 702 may be configured to receive photons from both the first source 706 and the second source 708. In contrast, the second detector 704 may be configured to detect photons from the second source 708 but not the first source 706. In various cases, a radiopharmaceutical is administered to the subject. The radiopharmaceutical accumulates in the first source 706 and the second source 708. A radionuclide of the radiopharmaceutical is configured to emit photons. During an acquisition period, for example, the first detector 702 may detect n photons, whereas the second detector 704 may detect m photons, wherein n and m are positive integers. Due to the known locations of the first source 706, the second source 708, the first field-of-view 710, and the second field-of-view 712, the photons attributed to the first source 706 and the second source 708 may be determined. For example, because the first source 706 and the second source 708 are located within the first field-of-view 710 of the first detector 702, the n photons detected by the first detector 702 may have originated from a combination of the first source 706 and the second source 708. However, because the first source 706 is outside of the second field-of-view 712, the m photons detected by the second detector 704 may have originated from the first source 706 and not the second source 708. In various examples, it may be inferred that the m photons were transmitted by the second source 708 and a portion of the n photons were transmitted by the first source 706.

The portion of the n photons that were transmitted by the first source 706 may be determined based on the sensitivity of the first detector 702 to the first source 706. The sensitivity of a detector to photons transmitted from a particular position (x, y, z) in a 3D space, for example, may be a positive number. A line-of-response (LOR) may be defined as a line segment extending from a particular position to the detector, wherein a photon transmitted from the particular position travels along the LOR in order to be received by the detector. The sensitivity of a detector to a position may be the sensitivity to an LOR extending from the position to the detector. In some implementations, the sensitivity of the detector may be between 0 and 1, wherein a sensitivity of 0 indicates that the detector is not capable of receiving any photons transmitted along the LOR associated with the position and a sensitivity of 1 indicates that the detector receives all photons transmitted along the LOR from the position.

Each detector may have a sensitivity to each coordinate in the 3D space. The sensitivity of an example detector may relate to the position of the field-of-view of the detector. For example, the detector may have minimal or no sensitivity to photons transmitted from positions outside of the field-of-view, and may have nonzero sensitivities to photons transmitted from positions inside of the field-of-view. In addition, the detector may have a higher sensitivity to a position that is relatively close to the detector than a position relatively far away from the detector. This may be because photons that are transmitted longer distances may be more likely to be scattered, absorbed, or otherwise attenuated prior to reaching the detector. Furthermore, the presence of attenuating structures along the LOR may impact the sensitivity (and may also impact the shape of the corresponding field-of-view of the detector). For example, the presence of a bone along the LOR may decrease the sensitivity. In general, the sensitivities of a detector to various positions (or LORs from those positions) within a body of a subject can be derived based on a scan representing the anatomy of the subject (e.g., a CT scan), the location of the detector with respect to the anatomy of the subject, the orientation of the detector with respect to the anatomy of the subject, the shape of the detector (e.g., a size of a pinhole of the detector), or a combination thereof. These factors may be related to the sensitivities by a computer model (e.g., a convolutional neural network (CNN) and/or Monte Carlo simulation), which can be precisely derived and/or trained via trends observed with other subjects and/or experimental phantoms.

In particular cases, the sensitivities are derived based on an anatomic model of the patient. An anatomic model of the patient can be generated based on an anatomic scan of the patient. The anatomic model may account for both the positions of structures-of-interest within the body, as well as sources of attenuation in the body. The anatomic scan (e.g., a CT scan) can be used to estimate attenuation (scatter and/or absorption) along a given line of response extending between regions within the body and detector positions. In various cases, the units represented in the anatomic scan (e.g., the Houndsfield units given in the CT scan) is converted to a linear attenuation coefficient for the photons that will be emitted from the radiopharmaceutical activity distribution. The amount of attenuation of a particular line-of-response is calculated based on the line integral of the attenuation associated with the line-of-response between the source and the detector.

In various implementations, Monte Carlo simulations are performed to determine the sensitivities of different detector positions to different regions within the body. For example, simulated photons originating from a given region are tracked through the body (which is defined based on the anatomic model of the body), and the number of the simulated photons that impact a given detector position corresponds to the sensitivity of the detector position to the region. In a specific instance, if the kidney emits one million photons in simulation, and the simulated detector detects 100 photons, the sensitivity of the detector to the kidney is 100/1,000,000. In various implementations, a PET image can be used to get an estimate of the expected uptake of the radiopharmaceutical in the different structures of interest (e.g., organs and/or tumors). Experimentally, Monte Carlo simulations were found to accurately model the impact of scatter within the body.

In various implementations, the sensitivities of a detector to various positions within a 3D space can be represented as a matrix or vector. In cases where there are multiple detectors, with respective sensitivities to positions within a 3D space, then a systems matrix P representing the respective sensitivities may be defined. For example, the systems matrix P may define the sensitivities of the detectors to locations of organs-of-interest within the 3D space. The number of photons detected by the detectors during an acquisition period may be represented in a data array g. In various cases, the radiation distribution f within the 3D space (e.g., within the organs-of-interest) can be calculated using the following Equation 1:

$$Pf = g \qquad \text{Equation 1}$$

In a simplified example related to FIG. 7, two positions within the 3D space of the environment 700 may be considered: the position of the first source 706 (a "first position") and the position of the second source 708 (a "second position"). The first detector 702 may have a sensitivity of a1 to the first position and a sensitivity of a2 to the second position. The second detector 704 may have a sensitivity of 0 to the first position (since the first position is outside of the second field-of-view 712) and a sensitivity of b2 to the second position. Thus, the systems matrix P for this simplified example may be defined as [[a1, a2], [0, b2]]. The g term may be defined as a two-element vector including m and n.

The radiation distribution at the first position and the second position (i.e., of the first source 706 and the second source 708) can therefore be calculated using Equation 1.

The relationship between the photon counts detected by the first detector 702 and the second detector 704 and the locations of the first source 706 and the second source 708 can be conceptualized in alternate ways. For example, a set of vectors may be defined based on the locations of the first source 706 and the second source 708 within the 3D space. A linear operator may be defined that takes the set of vectors to a space of photon counts (i.e., measurements by the first detector 702 and the second detector 704). The radiation distributions at the first position and the second position can be calculated by performing an inversion of the linear operator.

Using the aforementioned techniques, the number of photons received by the first detector 702 from the first source 706 and the second source 708, as well as the number of photons received by the second detector 704 from the second source 708, can be derived. In various implementations, the amount of radionuclide that has decayed within the first source 706 and the second source 708 during the acquisition period can be derived based on the number of received photons attributed to the first source 706 and the second source 708. That is, each photon detected by the first detector 702 and the second detector 704 represents a particle of radionuclide decaying. In various implementations, not all photons emitted from decaying radionuclides by the first source 706 or the second source 708 are detected by the first detector 702 or the second detector 706. For example, a radionuclide particle in the first source 706 could decay and transmit a photon in an LOR that is not terminated by either one of the first detector 702 or the second detector 704. The total amount of radionuclide that has decayed in the first source 706 and the second source 708 (e.g., f in Equation 1) may be determined based on the photon counts detected by the first detector 702 and the second detector 704, as well as the geometry of the environment 700. The amount of radionuclide that has decayed in different positions within the environment 700 can be referred to as the "radiation distribution" within the environment 700.

The radiation distribution within the environment 700 can be used to determine the radiation dosages to one or more organs in the environment 700. In various cases, the radiation dosage at a particular location in space due to a decaying radionuclide at another location in the space is based on the distance between the locations. Based on the radiation distribution within the subject, and the locations of the organs-of-interest within the subject, the radiation dosages of the organs-of-interest can be derived. According to some implementations, the radiation distribution across structures within the environment is estimated based on the photon counts detected by the detectors 702 and 704. Due to the physics of radioactive decay, it may be inferred that the photon counts detected by the detectors 702 and 704 will decrease over time (e.g., in subsequent acquisition periods). The photon counts from multiple acquisition periods can be acquired, and a plot of photon count over time can be generated based on the photon counts detected by the detectors 702 and 704. The radiation dosage can be calculated based on the area under the curve of the plot of photon count over time. In some examples, the radiation dosage is further calibrated by a qualified care provider according to industry standards.

Figure 8:
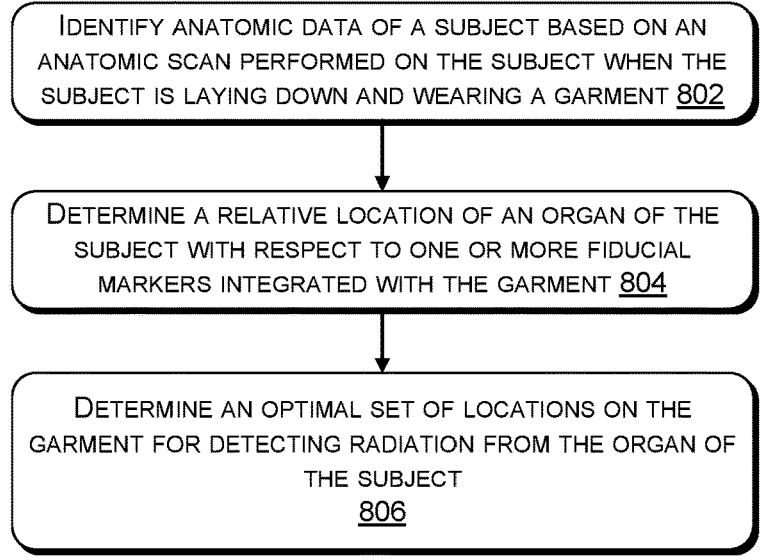
FIG. 8 illustrates an example process for optimizing the locations of detectors on a garment.

FIG. 8 illustrates an example process 800 for optimizing the locations of detectors on a garment. The process 800 may be performed by an entity, such as a processor, a computing device, a scanner, or a combination thereof.

At 802, the entity identifies anatomic data of a subject based on an anatomic scan performed on the subject when the subject is lying down and wearing a garment. The subject, for example, may be a patient. The anatomic scan may be a CT scan and/or a PET-CT scan of the subject. For example, the PET-CT scan may be performed when the subject is dosed with a positron emitter targeting a receptor for a radiopharmaceutical. The PET-CT scan may confirm that the subject includes one or more tumors that express the receptor.

The garment may at least partially be disposed around a torso of the subject. In various implementations, the garment includes a wrap (e.g., a fabric strap disposed around the subject). The garment may further include one or more fiducial markers integrated with the wrap. The fiducial marker(s) may include a material configured to attenuate x-rays used to generate the CT scan and/or PET-CT scan, such as a metal (e.g., gold), carbon, or x-ray attenuating polymer. In various implementations, the garment includes a shell, which may have a surface that is contoured to a shape of the subject. The shell may include one or more panels integrated with the garment, or may include a single component that is configured to support the weight of the subject when the subject is lying down. In some cases, the shell includes at least one of polystyrene foam, silicon, or fiberglass. In some cases, the garment is a vest worn by the subject.

At 804, the entity determines a relative location of an organ of the subject with respect to the one or more fiducial markers integrated with the garment. According to various implementations, the anatomic scan of the subject indicated in the anatomic data may include a 3D image of the subject and the garment. The image may be manually and/or automatically segmented, such that an outer boundary of a depiction of the organ may be identified within the image. In some implementations, one or more tumors within the subject are also segmented.

At 806, the entity determines a set of optimal locations on the garment for detecting radiation from the organ of the subject. In various implementations, the entity assigns a predetermined number (e.g., a number greater than or equal to 10 and less than or equal to 15) of detectors the optimal positions on the garment for detecting radiation from the organ, such that the entity determines the predetermined number of optimal positions on the garment. For example, the positions may be associated with fields-of-view that include the location of the organ and/or excludes the location(s) of the tumor(s). In some implementations, the entity further determines a pinhole size of each detector that corresponds to a field-of-view that includes the location of the organ and/or excludes the location(s) of the tumor(s).

In some implementations, the entity determines the set of optimal locations, based at least in part, on a PET scan of the subject. The PET scan, for example, may be obtained while the subject is dosed with a positron emitter that targets the receptor of the tumor(s) to be treated. The PET scan provides an estimate of the density of receptors on the tumors and also the expected uptake of a radiopharmaceutical targeting the receptors in the organs. This may be indicative of the expected activity of the radiopharmaceutical when the subject is administered a dose of the radiopharmaceutical. Thus, the anatomic data is indicative of the size and location of different regions-of-interest (e.g., tumors and/or organs) within the subject, and the PET scan provides information about the expected uptake into different regions-of-interest.

According to various implementations, the garment may be customized for the subject. For example, detectors may be fastened or otherwise placed at the set of optimal locations on the garment.

Figure 9:
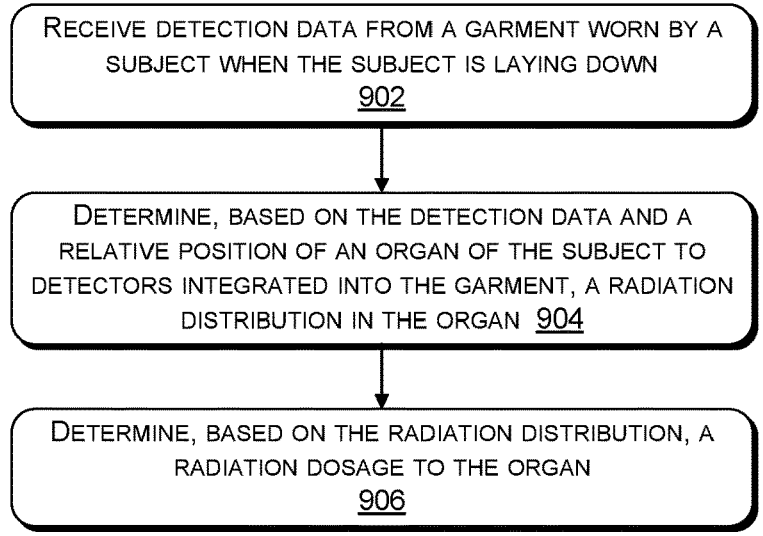
FIG. 9 illustrates an example process or determining a radiation dosage to an organ of a subject who has been dosed with a radiopharmaceutical.

FIG. 9 illustrates an example process 900 for determining a radiation dosage to an organ of a subject who has been dosed with a radiopharmaceutical. The process 900 may be performed by an entity, such as a processor, a computing device, a scanner, or a combination thereof.

At 902, the entity receives detection data from a garment worn by a subject when the subject is lying down. In various cases, the subject may have received a dose of a radiopharmaceutical. In various implementations, the detection data is generated based on photons detected from the radiopharmaceutical by a set of detectors integrated within the garment during at least one acquisition period. The fields-of-view of the detectors may include an organ of the subject.

The garment may at least partially be disposed around a torso of the subject. In various implementations, the garment includes a wrap (e.g., a fabric strap disposed around the subject). The garment may further include one or more fiducial markers integrated with the wrap. The fiducial marker(s) may include a material configured to attenuate x-rays used to generate the CT scan and/or PET-CT scan, such as a metal (e.g., gold), carbon, or x-ray attenuating polymer. In various implementations, the garment includes a shell, which may have a surface that is contoured to a shape of the subject. The shell may include one or more panels integrated with the garment, or may include a single component that is configured to support the weight of the subject when the subject is lying down. In some cases, the shell includes at least one of polystyrene foam, silicon, or fiberglass. In some cases, the garment is a vest worn by the subject.

According to some cases, the detection data is transmitted wirelessly to the entity from the garment. For example, the garment and the subject may be located remotely from the entity performing the example process 900. In some cases, the subject is located at their residence, whereas the entity performing the example process 900 may be located at a clinical environment (e.g., a hospital).

At 904, the entity determines, based on the detection data and a relative position of an organ of the subject to detectors integrated into the garment, a radiation distribution in the organ. The relative locations, in various examples, may be determined based on an anatomic scan (e.g., a CT scan) of the subject while the subject is wearing the garment.

In some cases, the entity defines a linear operator that takes a set of vectors to a space of the detected photons in the detection data. The set of vectors may be indicative of the organs of the subject. The radiation distribution and/or radiation dosage to the organ may be determined by performing an inversion of the linear operator.

In various implementations, the entity identifies, stores, or generates a systems matrix that includes sensitivities of the detectors to LORs extending from the organ. The entity may determine a dosage array based on the systems matrix and a data array that includes counts of the photons detected by the detectors.

At 906, the entity determines, based on the radiation distribution in the organ, a radiation dosage to the organ. For example, the photons transmitted from the organ may expose the organ to ionizing radiation that impacts the radiation dosage to the organ. In some implementations, the radiation dosage to the organ can be derived based on detection data acquired by the garment during multiple acquisition periods after the subject has been dosed with the radiopharmaceutical. In some cases, the subject has received multiple doses of the radiopharmaceutical. The radiation dosage to the organ may therefore be determined based on radiation distributions in the organ determined over multiple acquisition periods during the multiple doses. According to various implementations, a care provider may determine whether to administer an additional dose of the radiopharmaceutical based on the cumulative radiation dosage to the organ.

Figure 10:
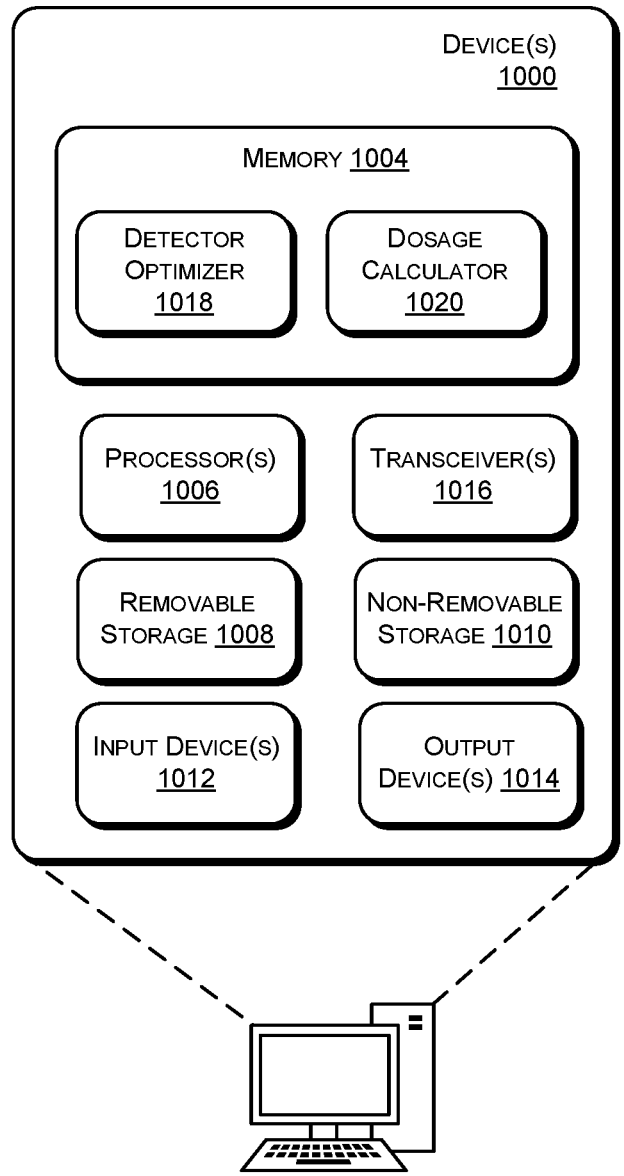
FIG. 10 illustrates an example of at least one device configured to perform one or more functions described herein.

FIG. 10 illustrates an example of at least one device 1000 configured to perform one or more functions described herein. The device(s) 1000 may be a computing device or medical device, such as the scanner 106 or computing device 110 illustrated in FIG. 1, the computing device 410 illustrated in FIG. 4, or any combination thereof. The device(s) 1000 includes any of memory 1004, processor(s) 1006, removable storage 1008, non-removable storage 1010, input device(s) 1012, output device(s) 1014, and transceiver(s) 1016. The device(s) 1000 may be configured to perform various methods and functions disclosed herein.

The memory 1004 may include one or more components. The component(s) 1018 may include at least one of instruction(s), program(s), database(s), software, operating system(s), etc. In some implementations, the component(s) include instructions that are executed by processor(s) 1006 and/or other components of the device(s) 1000. For example, the memory 1004 may store a detection optimizer 1018, which includes instructions, that when executed by the processor(s) 1006, cause the processor(s) 1006 to perform operations including determining a set of optimal positions for detectors in a garment based on anatomic data. In some implementations, the memory 1004 stores a dosage calculator 1020 that, when executed by the processor(s) 1006, causes the processor(s) 1006 to perform operations including determining a radiation dosage to an organ based on detection data from a garment.

In some implementations, the processor(s) 1006 include a central processing unit (CPU), a graphics processing unit (GPU), or both CPU and GPU, or other processing unit or component known in the art.

The device(s) 1000 may also include additional data storage devices (removable and/or non-removable) such as, for example, magnetic disks, optical disks, or tape. Such additional storage is illustrated in FIG. 10 by removable storage 1008 and non-removable storage 1010. Tangible computer-readable media can include volatile and non-volatile, removable and non-removable media implemented in any method or technology for storage of information, such as computer readable instructions, data structures, program modules, or other data. The memory 1004, the removable storage 1008, and the non-removable storage 1010 are all examples of computer-readable storage media. Computer-readable storage media include, but are not limited to, Random Access Memory (RAM), Read-Only Memory (ROM), Electrically Erasable Programmable Read-Only Memory (EEPROM), flash memory, or other memory technology, Compact Disk Read-Only Memory (CD-ROM), Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device 1000. Any such tangible computer-readable media can be part of the device 1000.

The device 1000 may be configured to communicate over a telecommunications network using any common wireless and/or wired network access technology. Moreover, the device 1000 may be configured to run any compatible device Operating System (OS), including but not limited to, Microsoft Windows Mobile, Google Android, Apple iOS, Linux Mobile, as well as any other common mobile device OS.

The device 1000 also can include input device(s) 1012, such as a keypad, a cursor control, a touch-sensitive display, voice input device, etc., and output device(s) 1014 such as a display, speakers, printers, etc. These devices are well known in the art and need not be discussed at length here.

As illustrated in FIG. 10, the device 1000 also includes one or more wired or wireless transceiver(s) 1016. For example, the transceiver(s) 1016 can include a network interface card (NIC), a network adapter, a Local Area Network (LAN) adapter, or a physical, virtual, or logical address to connect to various network components, for example. To increase throughput when exchanging wireless data, the transceiver(s) 1016 can utilize multiple-input/multiple-output (MIMO) technology. The transceiver(s) 1016 can include any sort of wireless transceivers capable of engaging in wireless, radio frequency (RF) communication. The transceiver(s) 1016 can also include other wireless modems, such as a modem for engaging in Wi-Fi, WiMAX, Bluetooth, infrared communication, and the like. The transceiver(s) 1016 may include transmitter(s), receiver(s), or both.

Example Clauses

1. A system, including: a garment including: a wrap configured to be worn by a subject when the subject is lying down; one or more fiducial markers integrated with the wrap, the one or more fiducial markers including a material configured to attenuate x-rays; detectors configured to be integrated with the wrap and to detect photons emitted by a radionuclide disposed inside of the subject; and a first transceiver configured to transmit detection data indicative of the photons detected by the detectors; a second transceiver configured to receive the detection data; at least one processor; and memory storing instructions that, when executed by the at least one processor, cause the at least one processor to perform operations including: identifying anatomic data of the subject indicating locations of organs of the subject with respect to the one or more fiducial markers integrated with the wrap when the wrap is worn by the subject and the subject is lying down; identifying positions of the detectors along the wrap; determining, based on the detection data, the anatomic data, and the positions of the detectors along the wrap, radiation dosages to the organs; and determining that the radiation dosages to the organs are below one or more thresholds; and outputting a message indicating that the radiation dosages are below the one or more thresholds.

2. The system of clause 1, wherein the garment includes: a shell including: a surface contoured around a shape of the torso of the subject; and at least one of polystyrene foam, fiberglass, or silicon; and fabric configured to at least partially wrap around a torso of the subject.

3. The system of clause 1 or 2, wherein determining, based on the detection data, the anatomic data, and the positions of the detectors along the wrap, the radiation dosages to the organs includes: generating, based on the position of the detectors relative to the organs, a systems matrix (P) including sensitivities of the detectors to the locations of the organs; generating, based on the detection data, a data array (g) including counts of the photons detected by the detectors; determine an dosage array (f) based on the following equation: Pf=g, and wherein f includes the radiation distribution within the organs; and determining the radiation dosages to the organs based on the radiation distribution within the organs.

4. The system of any one of clauses 1 to 3, further including: a computed tomography (CT) scanner configured to generate the anatomic data by performing a CT scan on the subject when the wrap is worn by the subject and the subject is lying down.

5. The system of clause 4, wherein the CT scanner includes a positron emission tomography (PET)-CT scanner configured to generate the anatomic data by performing a PET-CT scan on the subject when the wrap is worn by the subject, the subject is lying down, and the subject is dosed with a radiolabel, the radiolabel including a positron emitter and a first binding domain specifically binding a receptor, and wherein a radiopharmaceutical includes the radionuclide, a second binding domain specifically binding the receptor, and a chelator that connects the radionuclide to the second binding domain.

6. A method, including: generating anatomic data by performing a computed tomography (CT) scan on a subject wearing a garment; identifying, based on the anatomic data, location of organs of the subject with respect to one or more fiducial markers integrated with the garment; determining, based on the location of the organs of the subject with respect to one or more fiducial markers of the garment, an optimal set of locations on the garment for detecting radiation from the organs of the subject; outputting the set of locations on the garment; receiving, from the garment, detection data indicating photons detected by detectors placed at the optimal set of locations on the garment when the subject is wearing the garment and has been dosed with a radiopharmaceutical targeting a receptor; and determining, based on the detection data, radiation dosages to the organs.

7. The method of clause 6, wherein the CT scan includes a positron emission tomography-CT (PET-CT) scan performed when the subject is dosed with a positron emitter targeting the receptor.

8. The method of clause 6 or 7, wherein the receptor includes a somastatin receptor, a prostate-specific membrane antigen (PSMA) receptor, or a thyroid cancer cell, and wherein the radiopharmaceutical includes $^{177}$Lu-DOTATATE, $^{68}$Ga-PSMA, $^{177}$Lu-PSMA, $^{131}$I, or $^{124}$I.

9. The method of any one of clauses 6 to 8, wherein the organs include at least one of a kidney, a liver, a spleen, or bone marrow.

10. The method of any one of clauses 6 to 9, wherein identifying, based on the anatomic data, locations of organs of the subject with respect to the one or more fiducial markers integrated with the garment includes segmenting depictions of the organs in the PET-CT scan.

11. The method of any one of clauses 6 to 10, wherein the garment includes a vest.

12. The method of any one of clauses 6 to 11, wherein the garment is disposed around an abdomen of the subject when the subject is wearing the garment.

13. The method of any one of clauses 6 to 12, wherein the subject is lying down when the subject is wearing the garment.

14. The method of any one of clauses 6 to 13, wherein the garment includes at least one of fabric, polystyrene foam, fiberglass, or silicon.

15. The method of any one of clauses 6 to 14, wherein the fiducial markers include a metal, carbon, or a polymer configured to attenuate x-rays.

16. The method of any one of clauses 6 to 15, wherein the set of optimal locations includes to 15 positions along the garment.

17. The method of any one of clauses 6 to 16, wherein the detectors include 10 to 15 detectors.

18. The method of any one of clauses 6 to 17, wherein determining, based on the detection data, radiation dosages to the organs includes: defining a linear operator that takes a set of $x_i$ vectors to a space of the measurements in the detection data, wherein the $x_i$ vectors are indicative of the locations of the organs of the subject; and determining the radiation dosages to the organs by performing an inversion of the linear operator.

19. The method of any one of clauses 6 to 18, wherein determining, based on the detection data, radiation dosages to the organs includes: generating, based on the positions of the detectors relative to the organs, a systems matrix (P) including sensitivities of the detectors to the locations of the organs; generating a data array (g) including counts of the photons detected by the detectors; determining an dosage array (f) based on the following equation: Pf=g, and wherein f includes the radiation distributions within the organs; and determining the radiation dosages to the organs based on the radiation distributions within the organs.

20. The method of any one of clauses 6 to 19, further including: determining, based on the anatomic data, locations of tumors of the subject with respect to the one or more fiducial markers, wherein determining the optimal set of locations on the garment for detecting radiation from the organs of the subject is further based on the locations of the tumors of the subject.

21. The method of any one of clauses 6 to 20, further including: determining, based on the anatomic data, optimal fields-of-view for the detectors; determining pinhole sizes corresponding to the optimal fields-of-view; and outputting the pinhole sizes.

22. The method of any one of clauses 6 to 21, wherein the detection data includes: first photon counts detected by the detectors at a first time; and second photon counts detected by the detectors at a second time.

23. The method of clause 22, wherein the first time and the second time are separated by about 24 hours.

24. The method of clause 22 or 23, further including: generating a photon count model based on a predetermined half-life of the radionuclide and at least one of the first photon counts or the second photon counts; determining that a difference between third photon counts detected by the detectors at a third time and the photon count model is greater than a threshold amount; and excluding the third photon counts from the detection data.

25. The method of any one of clauses 6 to 24, the detection data being first detection data indicating photons detected by the detectors when the subject has a first dose of the radionuclide targeting the receptor, the radiation dosages being first radiation dosages, the method further including: receiving, from the garment, second detection data indicating photons detected by the detectors when the subject is wearing the garment and has a second dose of the radionuclide targeting the receptor; determining, based on the second detection data, second radiation dosages to the organs; and determining total radiation dosages to the organs by adding the first radiation dosages and the second radiation dosages.

26. The method of clause 25, further including: receiving, from a care provider, an indication of threshold radiation dosages; determining that the total radiation dosages are less than the threshold radiation dosages; and outputting a message indicating that the total radiation dosages are less than the threshold radiation dosages.

27. The method of any one of clauses 6 to 26, the anatomic data being first anatomic data, the locations of the organs being first locations of the organs, the method further including: in response to receiving the first detection data, generating second anatomic data by performing a CT scan on the subject when the subject is wearing a garment; identifying, based on the second anatomic data, second locations of the organs of the subject with respect to one or more fiducial markers integrated with the garment, wherein determining the second radiation dosages to the organs is further based on the second locations of the organs.

28. A garment, including: a wrap configured to be worn by an subject when the subject is lying down; one or more fiducial markers integrated with the wrap, the one or more fiducial markers including a material configured to attenuate x-rays; detectors integrated with the wrap and configured to detect photons emitted by a radionuclide; one or more batteries configured to supply electrical power to the detectors; and a transceiver configured to transmit data indicative of the photons to an external device.

29. The garment of clause 28, further including: a shell including a surface contoured to a shape of the subject.

30. The garment of clause 29, wherein the shell includes at least one of polystyrene foam, fiberglass, or silicon.

31. The garment of any one of clauses 28 to 30, wherein the wrap includes: fabric configured to at least partially wrap around a torso of the subject.

32. A method, including: identifying anatomic data of a subject who is dosed with a positron emitter targeting a receptor and who is wearing a garment, the anatomic data being based on a computed tomography (CT) scan performed on the subject; determining, based on the anatomic data, a location of an organ of the subject with respect to one or more fiducial markers integrated with the garment; determining, based on the location of the organ of the subject with respect to the one or more fiducial markers of the garment, an set of optimal locations on the garment for detecting radiation from the organ of the subject; and outputting the set of optimal locations on the garment.

33. The method of clause 32, wherein the organ includes a kidney, a liver, a spleen, or bone marrow of the subject.

34. The method of clause 32 or 33, wherein identifying, based on the anatomic data, the locations of the organ of the subject with respect to the one or more fiducial markers integrated with the garment includes segmenting a depiction of the organ in the CT scan.

35. The method of any one of clauses 32 to 34, wherein the CT scan includes a positron emission tomography-CT (PET-CT) scan.

36. The method of any one of clauses 32 to 35, further including: determining, based on the anatomic data, a location of a tumor of the subject with respect to the one or more fiducial markers, wherein determining the set of optimal locations on the garment for detecting radiation from the organs of the subject is further based on the location of the tumor of the subject and an expected binding of the therapy agent to the organs and tumors in the subject.

37. The method of any one of clauses 32 to 36, further including: determining, based on the anatomic data, an optimal field-of-view for a detector positioned at one of the optimal locations; determining a pinhole size corresponding to the optimal field-of-view; and outputting the pinhole size.

38. The method of any one of clauses 32 to 37, wherein the set of optimal locations includes 10 to 15 positions along the garment.

39. A method, including: receiving, from a garment, detection data indicating photon counts detected by detectors integrated into a garment worn by a subject when the subject is lying down and has been dosed with a radionuclide; identifying a relative position of an organ of the subject to the detectors integrated into the garment worn by the subject; determining, based on the detection data and the relative position of the organ to the detectors, a radiation dosage to the organ; comparing the radiation dosage to a threshold; and based on comparing the radiation dosage to the threshold, outputting a message indicating whether the radiation dosage to the organ is below the threshold.

40. The method of clause 39, wherein the detection data includes: first photon counts detected by the detectors at a first time; and second photon counts detected by the detectors at a second time.

41. The method of clause 40, wherein the first time and the second time are separated by about 24 hours.

42. The method of clause 40 or 41, further including: generating a photon count model based on a predetermined half-life of the radionuclide and at least one of the first photon counts or the second photon counts; determining that a difference between third photon counts detected by the detectors at a third time and the photon count model is greater than a threshold amount; and based on determining that the difference is greater than the threshold amount, excluding the third photon counts from the detection data.

43. The method of any one of clauses 39 to 42, the detection data being first detection data indicating photons detected by the detectors when the subject has a first dose of a radiopharmaceutical targeting a receptor, the radiopharmaceutical including the radionuclide, the radiation dosages being first radiation dosages, the method further including: receiving, from the garment, second detection data indicating photons detected by the detectors when the subject is wearing the garment and has a second dose of the radiopharmaceutical targeting the receptor; determining, based on the second detection data, a second radiation dosage to the organ; and determining a total radiation dosage to the organ by adding the first radiation dosage and the second radiation dosage.

44. The method of clause 43, the anatomic data being first anatomic data, the location of the organ being a first location of the organ, the method further including: in response to receiving the first detection data, generating second anatomic data by performing a CT scan on the subject when the subject is wearing the garment; and identifying, based on the second anatomic data, a second locations of the organ of the subject with respect to one or more fiducial markers integrated with the garment, wherein determining the second radiation dosage to the organ is based on the second location of the organ.

45. The method of any one of clauses 39 to 44, wherein determining, based on the detection data and the relative position of the organ to the detectors, the radiation dosage to the organ includes: defining a linear operator that takes a set of $x_i$ vectors to a space of the measurements in the detection data, wherein the $x_i$ vectors are indicative of the locations of the organs of the subject; and determining the radiation dosages to the organs by performing an inversion of the linear operator.

46. The method of any one of clauses 39 to 45, wherein determining, based on the detection data and the relative position of the organ to the detectors, the radiation dosage to the organ includes: generating, based on the position of the detectors relative to the organ, a systems matrix (P) including sensitivities of the detectors to the location of the organ; generating, based on the detection data, a data array (g) including counts of the photons detected by the detectors; determining a dosage array (f) based on the following equation: Pf=g, and wherein f includes the radiation distribution within the organ; and determining the radiation dosage to the organ based on the radiation distribution within the organ.

47. The method of any one of clauses 39 to 46, wherein the organ includes a kidney, a liver, a spleen, or bone marrow of the subject.

48. A system, including: at least one processor; and memory storing instructions that, when executed by the at least one processor, cause the at least one processor to perform operations including the method of any one of clauses 6 to 27 or 32 to 47.

49. A non-transitory computer-readable medium including instructions for performing the method of any one of clauses 6 to 27 or 32 to 47.

50. A method, including: receiving, from a garment, detection data indicating photon counts detected by detectors integrated into a garment worn by the subject when the subject is lying down and has received a first dose of a radionuclide; determining, based on the detection data, a radiation dosage from the first dose of the radionuclide to an organ of the subject; determining that the radiation dosage is below a threshold; and based on determining that the radiation dosage is below the threshold, administering a second dose of the radionuclide to the subject.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof. This disclosure cites to multiple patent documents, articles, and other references, all of which are incorporated by reference herein in their entirety.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, the practice of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

Certain implementations are described herein, including the best mode known to the inventors for carrying out implementations of the disclosure. Of course, variations on these described implementations will become apparent to those of ordinary skill in the art upon reading the foregoing description. The inventors expect skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

What is claimed is:

1. A system, comprising:
    a garment comprising:
        a wrap configured to be worn by a subject when the subject is lying down;
        one or more fiducial markers integrated with the wrap, the one or more fiducial markers comprising a material configured to attenuate x-rays;
        detectors configured to be integrated with the wrap and to detect photons emitted by a radionuclide disposed inside of the subject; and
        a first transceiver configured to transmit detection data indicative of the photons detected by the detectors;
    a second transceiver configured to receive the detection data;
    at least one processor; and
    memory storing instructions that, when executed by the at least one processor, cause the at least one processor to perform operations comprising:
        identifying anatomic data of the subject indicating locations of organs of the subject with respect to the one or more fiducial markers integrated with the wrap when the wrap is worn by the subject and the subject is lying down;
        identifying positions of the detectors along the wrap;
        determining, based on the detection data, the anatomic data, and the positions of the detectors along the wrap, radiation dosages to the organs; and
        determining that the radiation dosages to the organs are below one or more thresholds; and
        outputting a message indicating that the radiation dosages are below the one or more thresholds.

2. The system of claim 1, wherein the garment comprises:
a shell comprising:
a surface contoured around a shape of a torso of the subject; and
at least one of polystyrene foam, fiberglass, or silicon; and
fabric configured to at least partially wrap around a torso of the subject.

3. The system of claim 1, wherein determining, based on the detection data, the anatomic data, and the positions of the detectors along the wrap, the radiation dosages to the organs comprises:
generating, based on the position of the detectors relative to the organs, a systems matrix (P) comprising sensitivities of the detectors to the locations of the organs;
generating, based on the detection data, a data array (g) comprising counts of the photons detected by the detectors;
determine an dosage array (f) based on the following equation:

$$Pf=g, \text{ and}$$

wherein f comprises a radiation distribution within the organs; and
determining the radiation dosages to the organs based on the radiation distribution within the organs.

4. The system of claim 1, further comprising:
a positron emission tomography (PET)-computed tomography (CT) scanner configured to generate the anatomic data by performing a PET-CT scan on the subject when the wrap is worn by the subject, the subject is lying down, and the subject is dosed with a radiolabel, the radiolabel comprising a positron emitter and a first binding domain specifically binding a receptor, and
wherein a radiopharmaceutical comprises the radionuclide, a second binding domain specifically binding the receptor, and a chelator that connects the radionuclide to the second binding domain.

5. A method, comprising:
generating anatomic data by performing a computed tomography (CT) scan on a subject wearing a garment;
identifying, based on the anatomic data, location of organs of the subject with respect to one or more fiducial markers integrated with the garment by segmenting depictions of the organs in the CT scan;
determining, based on the location of the organs of the subject with respect to one or more fiducial markers of the garment, an optimal set of locations on the garment for detecting radiation from the organs of the subject;
outputting the set of locations on the garment;
receiving, from the garment, detection data indicating photons detected by detectors placed at the optimal set of locations on the garment when the subject is wearing the garment and has been dosed with a radiopharmaceutical targeting a receptor; and
determining, based on the detection data, radiation dosages to the organs.

6. The method of claim 5, wherein the CT scan comprises a positron emission tomography-CT (PET-CT) scan performed when the subject is dosed with a positron emitter targeting the receptor.

7. The method of claim 5, wherein the receptor comprises a somastatin receptor, a prostate-specific membrane antigen (PSMA) receptor, or a thyroid cancer cell, and
wherein the radiopharmaceutical comprises $^{177}$Lu-DOTATATE, $^{68}$Ga-PSMA, $^{177}$Lu-PSMA, $^{131}$I, or $^{124}$I.

8. The method of claim 5, wherein the organs comprise at least one of a kidney, a liver, a spleen, or bone marrow.

9. The method of claim 5, wherein the subject is lying down when the subject is wearing the garment.

10. The method of claim 5, wherein the set of optimal locations comprises 10 to 15 positions along the garment, and
wherein the detectors comprise 10 to 15 detectors.

11. The method of claim 5, wherein determining, based on the detection data, radiation dosages to the organs comprises:
defining a linear operator that takes a set of $x_i$ vectors to a space of measurements in the detection data, wherein the $x_i$ vectors are indicative of the locations of the organs of the subject; and
determining the radiation dosages to the organs by performing an inversion of the linear operator.

12. The method of claim 5, wherein determining, based on the detection data, radiation dosages to the organs comprises:
generating, based on positions of the detectors relative to the organs, a systems matrix (P) comprising sensitivities of the detectors to the locations of the organs;
generating a data array (g) comprising counts of the photons detected by the detectors;
determining an dosage array (f) based on the following equation:

$$Pf=g, \text{ and}$$

wherein f comprises a radiation distributions within the organs; and
determining the radiation dosages to the organs based on the radiation distributions within the organs.

13. The method of claim 5, further comprising:
determining, based on the anatomic data, locations of tumors of the subject with respect to the one or more fiducial markers,
wherein determining the optimal set of locations on the garment for detecting radiation from the organs of the subject is further based on the locations of the tumors of the subject.

14. The method of claim 5, further comprising:
determining, based on the anatomic data, optimal fields-of-view for the detectors;
determining pinhole sizes corresponding to the optimal fields-of-view; and
outputting the pinhole sizes.

15. The method of claim 5, wherein the detection data comprises:
first photon counts detected by the detectors at a first time; and
second photon counts detected by the detectors at a second time, and
wherein the method further comprises:
generating a photon count model based on a predetermined half-life of the radiopharmaceutical and at least one of the first photon counts or the second photon counts;
determining that a difference between third photon counts detected by the detectors at a third time and the photon count model is greater than a threshold amount; and
excluding the third photon counts from the detection data.

16. The method of claim 5, the detection data being first detection data indicating photons detected by the detectors when the subject has a first dose of the radionuclide targeting the receptor, the radiation dosages being first radiation dosages, the method further comprising:

receiving, from the garment, second detection data indicating photons detected by the detectors when the subject is wearing the garment and has a second dose of the radiopharmaceutical targeting the receptor;

determining, based on the second detection data, second radiation dosages to the organs; and determining total radiation dosages to the organs by adding the first radiation dosages and the second radiation dosages.

17. The method of claim 16, further comprising:

receiving, from a care provider, an indication of threshold radiation dosages;

determining that the total radiation dosages are less than the threshold radiation dosages; and outputting a message indicating that the total radiation dosages are less than the threshold radiation dosages.

18. The method of claim 16, the anatomic data being first anatomic data, the locations of the organs being first locations of the organs, the method further comprising:

in response to receiving the first detection data, generating second anatomic data by performing a CT scan on the subject when the subject is wearing a garment identifying, based on the second anatomic data, second locations of the organs of the subject with respect to one or more fiducial markers integrated with the garment, wherein determining the second radiation dosages to the organs is further based on the second locations of the organs.

19. A garment, comprising:

a wrap configured to be worn by a subject when the subject is lying down, the wrap comprising fabric configured to at least partially wrap around a torso of the subject;

a shell comprising a surface contoured to a shape of the subject;

one or more fiducial markers integrated with the wrap, the one or more fiducial markers comprising a material configured to attenuate x-rays;

detectors integrated with the wrap and configured to detect photons emitted by a radionuclide;

one or more batteries configured to supply electrical power to the detectors; and a transceiver configured to transmit data indicative of the photons to an external device.

20. The garment of claim 19, wherein the shell comprises at least one of polystyrene foam, fiberglass, or silicon.

* * * * *